US009649352B2

(12) United States Patent
Rafai Far et al.

(10) Patent No.: US 9,649,352 B2
(45) Date of Patent: May 16, 2017

(54) HIGH PURITY ORITAVANCIN AND METHOD OF PRODUCING SAME

(71) Applicants: The Medicines Company, Parsippany, NJ (US); AbbVie Inc., Chicago, IL (US)

(72) Inventors: Adel Rafai Far, Mount-Royal (CA); Gopal Krishna, Parsippany, NJ (US); Min Ding, Parsippany, NJ (US); Sanjay R. Chemburkar, North Chicago, IL (US); Carl M. Knable, North Chicago, IL (US); James P. Petzel, North Chicago, IL (US); Julie J. Pruyne, North Chicago, IL (US); Douglas M. Reamer, North Chicago, IL (US)

(73) Assignees: THE MEDICINES COMPANY, Parsippany, NJ (US); ABBVIE INC., Chicago, IL (US)

( * ) Notice: Subject to any disclaimer, the term of this patent is extended or adjusted under 35 U.S.C. 154(b) by 0 days.

(21) Appl. No.: 14/801,303

(22) Filed: Jul. 16, 2015

(65) Prior Publication Data

US 2016/0015772 A1    Jan. 21, 2016

Related U.S. Application Data

(60) Provisional application No. 62/025,737, filed on Jul. 17, 2014.

(51) Int. Cl.
*A61K 38/14* (2006.01)
*A61K 9/19* (2006.01)
*A61K 47/26* (2006.01)

(52) U.S. Cl.
CPC ........... *A61K 38/14* (2013.01); *A61K 9/19* (2013.01); *A61K 47/26* (2013.01)

(58) Field of Classification Search
None
See application file for complete search history.

(56) References Cited

U.S. PATENT DOCUMENTS

| | | | | |
|---|---|---|---|---|
| 5,840,684 A | * | 11/1998 | Cooper | C07K 9/008 514/2.4 |
| 7,119,061 B2 | | 10/2006 | Stogniew | |
| 8,420,592 B2 | * | 4/2013 | Lehoux | A61K 38/14 514/1.1 |
| 2011/0201546 A1 | | 8/2011 | Lehoux et al. | |

FOREIGN PATENT DOCUMENTS

WO    2010-129233    11/2010

OTHER PUBLICATIONS

Van Bambeke et al., 'Cellular pharmacokinetics and pharmacodynamics of the glycopeptide antibiotic oritavancin (LY333328) in a model of J774 mouse macrophages', Antimicrobial Agents and Chemotherapy, vol. 48, No. 8, pp. 2853-2860 (2004).
International Search Report issued Oct. 6, 2015 in corresponding International Application No. PCT/US2015/040736.
Written Opinion of the International Searching Authority issued Oct. 6, 2015 in corresponding International Application No. PCT/US2015/040736.

* cited by examiner

*Primary Examiner* — James H Alstrum Acevedo
*Assistant Examiner* — Roy Teller
(74) *Attorney, Agent, or Firm* — Wenderoth, Lind & Ponack, LLP

(57) ABSTRACT

Drug substance preparations of oritavancin having high purity are disclosed, along with pharmaceutical compositions comprising such oritavancin drug substance preparations, and drug products or dosage forms comprising such pharmaceutical compositions.

15 Claims, 7 Drawing Sheets

Figure 4 - Nucleus Factor B Diacetate Salt Flow Diagram
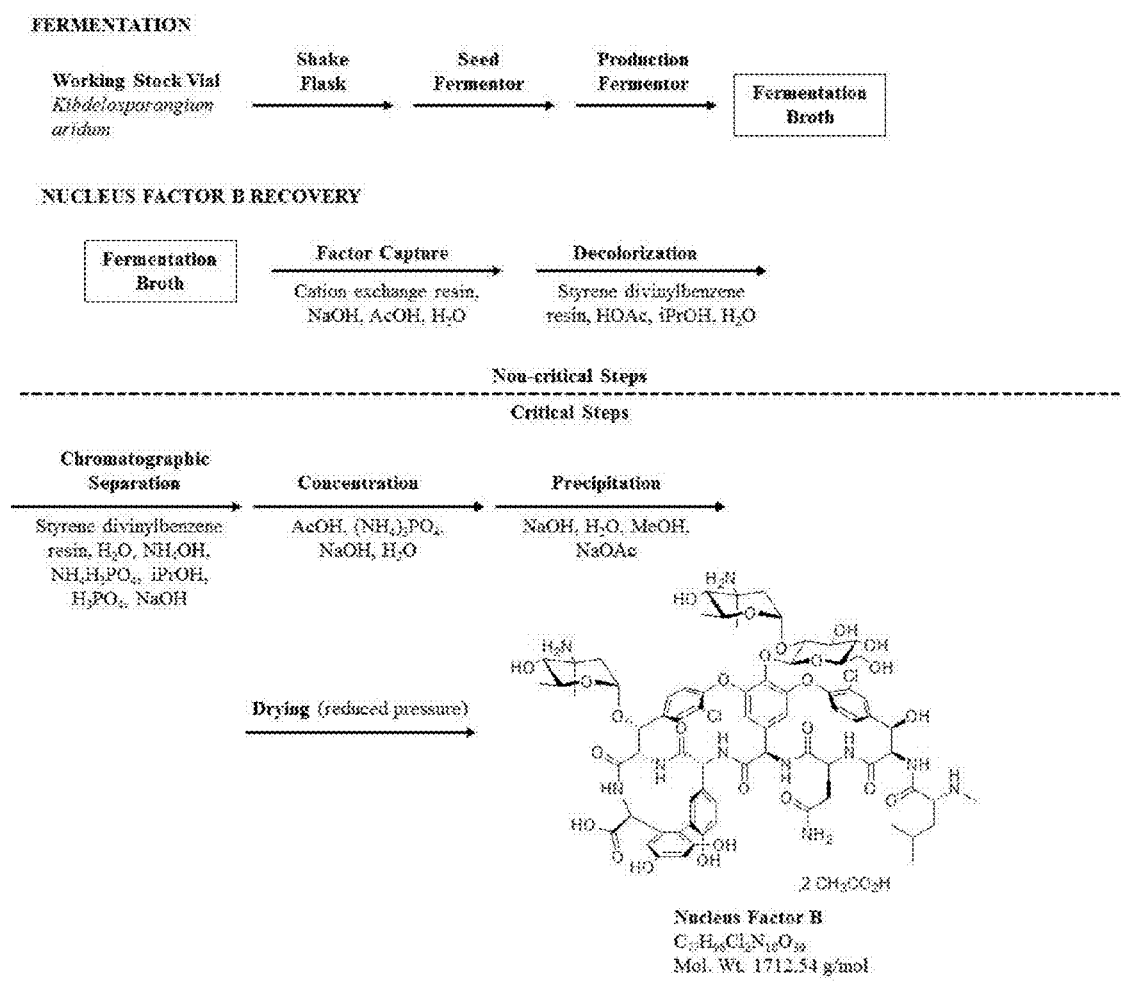

Figure 5 - Oritavancin Drug Substance Chemistry Flow Diagram
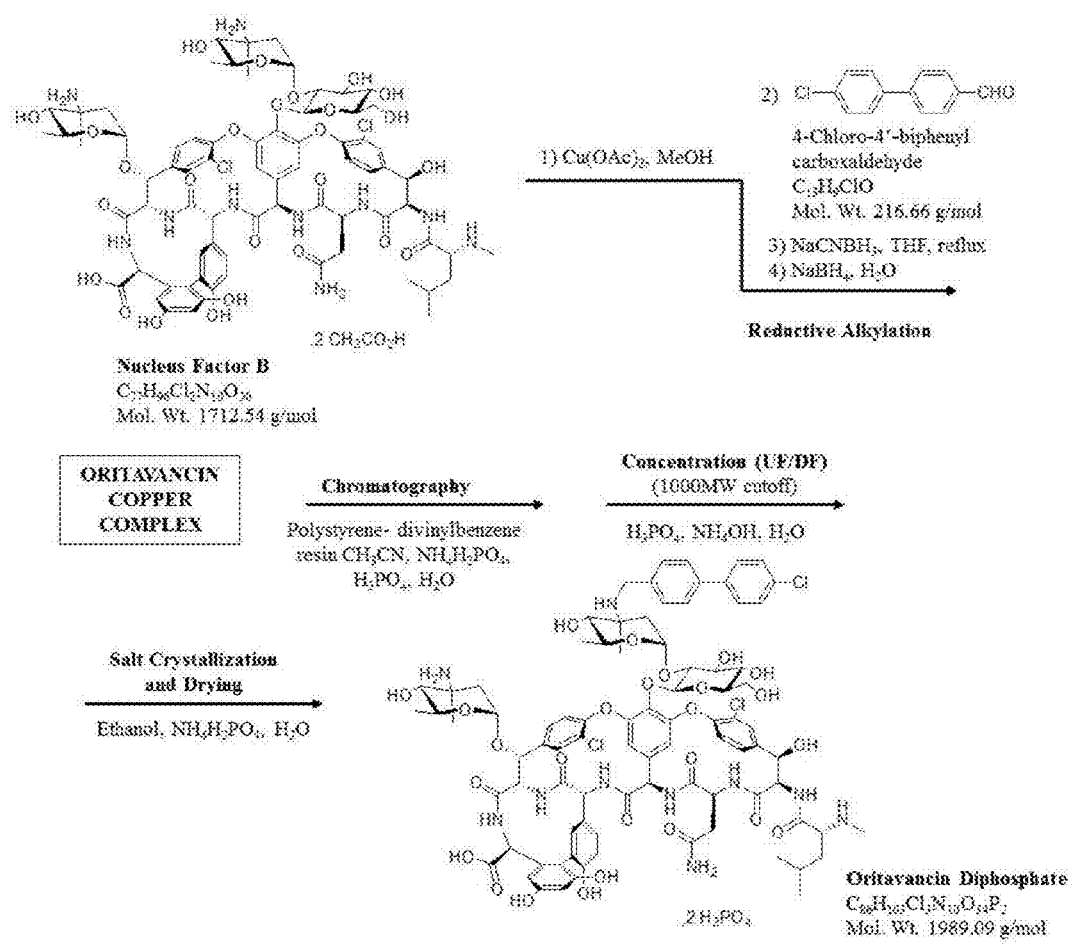

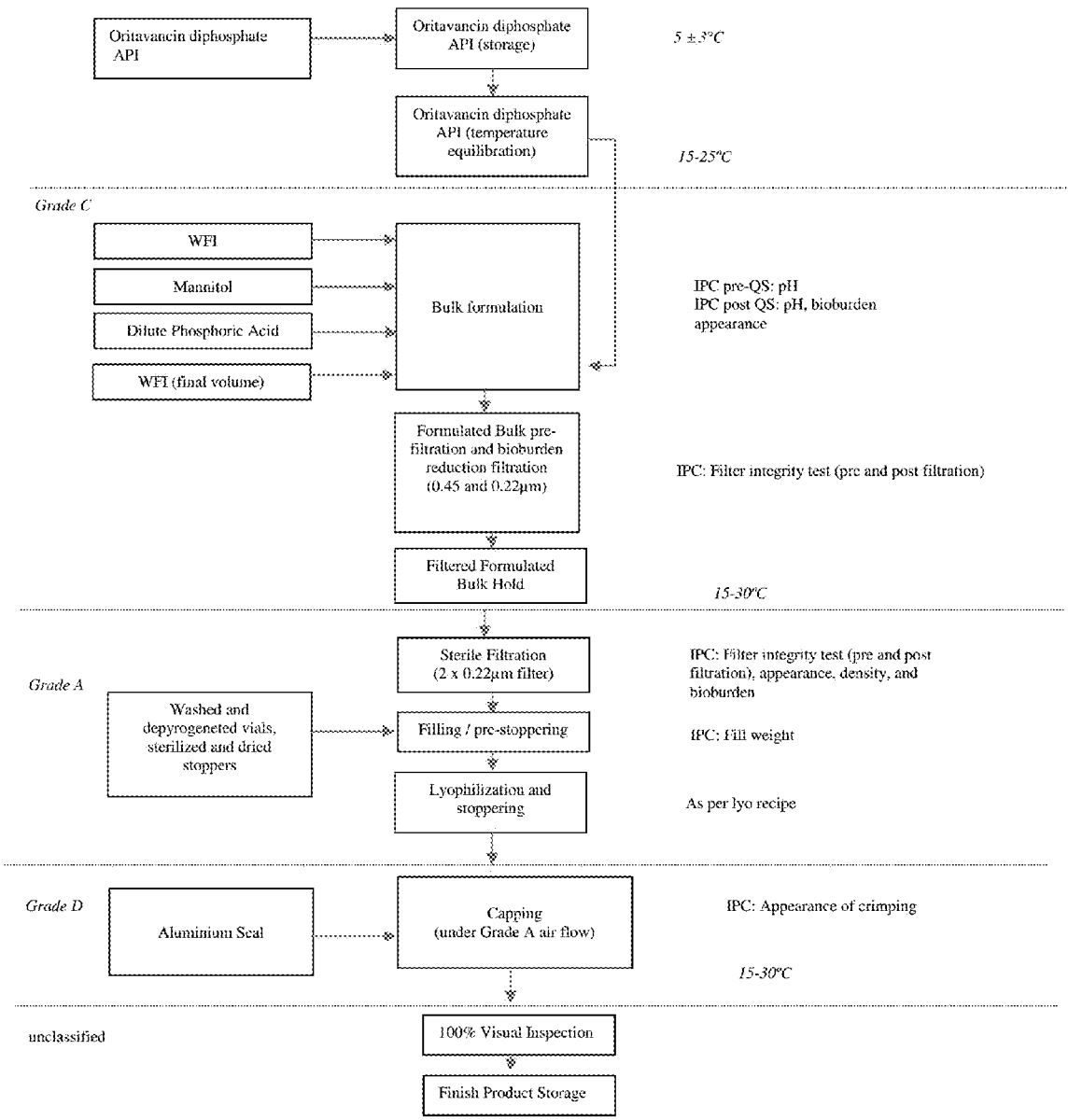
Figure 6 - Schematic Process Flow Diagram of Manufacturing Process

HIGH PURITY ORITAVANCIN AND METHOD OF PRODUCING SAME

BACKGROUND OF INVENTION

Pharmaceutical products for administration to subjects such as humans must contain high purity drug substance preparations and pharmaceutical compositions, and be formulated into dosage forms that contain consistent amounts of an active pharmaceutical ingredient (API).

All drug substance preparations, regardless of the API, contain varying amounts of impurities. These impurities can generally be grouped into categories based on their chemical identity and include "product-related impurities", i.e., impurities that are structurally similar to the API (e.g., enantiomers) and "process-related impurities", i.e. impurities introduced by or resulting from the processes used to make the API.

The identification, quantification, and qualification of impurities in pharmaceutical products, especially drug substances and pharmaceutical compositions made therefrom, is a critical aspect of ensuring the safety, efficacy and consistency of chemotherapeutic treatments. However, the characterization of impurities can be particularly difficult to achieve when drug substance preparations are obtained through the use of biological processes, such as fermentation, which are less predictable and controllable than wholly synthetic processes. Biological processes often utilize live prokaryotic or eukaryotic cells to produce a drug substance of interest, and large and intricate sets of impurities can be associated with the often structurally complex substances that are produced. In practice, it is very difficult to fully characterize all potential impurities and understand what impact they might have on safety and efficacy when a drug substance preparation is incorporated into pharmaceutical products. Therefore, the safest path is to minimize impurities in drug substances of interest.

The problematic nature of impurities is particularly acute for dalbaheptides, a class of complex glycopeptide antibiotics related to vancomycin that are important antibacterial agents for patients and healthcare providers facing challenges with the declining number of effective treatments available for bacterial infections. For example, vancomycin was approved for commercialization in the late 1950's, but it was relatively unused until the 1980's, largely in part because of perceived toxicity, and in particular nephrotoxicity and ototoxicity. It is now understood that the reported side effects were due to higher levels of impurities in early lots of the drug, which disappeared with improvements to purity (Moellering, R. C. Jr., *Clin. Infect. Dis.* 2006, 42, S3; Levine, D. P., *Clin. Infect. Dis.* 2006, 42, S5).

The importance of highly controlled purification of compounds in this class is further demonstrated by the fact that small changes in chemical structure can lead to drug substance preparations with widely different safety and/or efficacy profiles. For example, rapid infusion of vancomycin into subjects has been associated with the "red man" syndrome, a histamine-like response characterized by a combination of erythema, pruritus, hypotension, and angioedema, which is not seen during infusion of the closely-related drug teicoplanin (Levine, D. P., *Clin. Infect. Dis.* 2006, 42, S5; Sahai. J. et al., *Antimicrob. Agents Chemother.* 1990, 34, 765). Similarly, televancin, another drug with a highly similar chemical structure, was shown to be teratogenic in animal models while both vancomycin and teicoplanin were non-teratogenic in the same models (Damodaran, S. E., Madhan, S. J., *Pharmacol. Pharmacother.* 2011, 2, 135).

Small changes in chemical structure can also lead to unforeseen impacts on antibacterial activity in terms of either spectrum or potency. For example, compound A40926 is closely related to teicoplanin but it is much less active against coagulase-negative staphylococci, whereas dalbavancin is more potent than teicoplanin by an order of magnitude against these same microorganisms (Malabarba, A., Goldstein, B. P. J., *Antimicrob. Chemother.* 2005, 55 Suppl. S2, ii15).

It is thus evident that the development of high purity drug substance preparations and pharmaceutical compositions comprising dalbaheptides for use in pharmaceutical products, with both a reduced number of impurities and a decreased amount of those impurities that cannot be completely removed, is an important goal. The present invention is directed to this and other important goals.

BRIEF SUMMARY OF INVENTION

The present invention generally relates to drug substance preparations of oritavancin having high purity, to pharmaceutical compositions comprising such oritavancin drug substance preparations, drug products or dosage forms comprising such pharmaceutical compositions, and methods of making the same, among other important embodiments of the invention.

In a first embodiment the invention is directed to an oritavancin drug substance preparation of oritavancin, or a salt thereof, having a maximum impurity level of not more than 2.1% by peak area of impurity 1 (oritavancin factor A) and impurity 7 (oritavancin factor C), defined by peak A of FIG. 1 and peak G of FIG. 2, respectively.

In a second embodiment the invention is directed to a method for preparing an oritavancin drug substance preparation of oritavancin, or a salt thereof, having a maximum impurity level of not more than 2.1% by peak area of impurity 1 and impurity 7, defined by peak A of FIG. 1 and peak G of FIG. 2, respectively, comprising the steps of:

a) growing a culture of a chloroeremomycin-producing microorganism under fermentative conditions in a medium free of animal-sourced material (ASM) and under conditions promoting biosynthesis of chloroeremomycin by the culture, b) recovering chloroeremomycin from fermentation broth of a) using a polymeric exchange resin, c) decolorizing the chloroeremomycin recovered in b) using a polymeric adsorbent resin, chromatographically separating the decolorized chloroeremomycin using a hydrophobic polymeric resin column, and precipitating the separated chloroeremomycin using an organic solvent, d) preparing a solution of the precipitated chloroeremomycin of c) and a copper salt in an organic solvent, reacting the solution with 4-chloro-4'-biphenyl carboxaldehyde, and precipitating oritavancin-copper complex from the solution using acetonitrile, e) de-complexing copper from the oritavancin-copper complex of d) by adding a aqueous acid and separating the de-complexed oritavancin using a polymeric hydrophobic resin, wherein the adding and separating are performed concurrently or sequentially, f) concentrating the oritavancin solution eluted from the resin in e), g) precipitating oritavancin from the concentrate of f) in aqueous ethanol, and h) drying the precipitated oritavancin, thereby preparing a preparing an oritavancin drug substance preparation of oritavancin, or a salt thereof, having a maximum impurity level of not more than 2.1% by peak area of impurity 1 and impurity 7, defined by peak A of FIG. 1 and peak G of FIG. 2, respectively.

In a third embodiment the invention is directed to an oritavancin drug substance preparation of oritavancin, or a salt thereof, having a maximum impurity level of not more than 2.1% by peak area of impurity 1 and impurity 7, defined by peak A of FIG. 1 and peak G of FIG. 2, respectively, prepared by a method comprising the steps of:
a) growing a culture of a chloroeremomycin-producing microorganism under fermentative conditions in a medium free of animal-sourced material (ASM) and under conditions promoting biosynthesis of chloroeremomycin by the culture,
b) recovering chloroeremomycin from fermentation broth of a) using a polymeric exchange resin,
c) decolorizing the chloroeremomycin recovered in b) using a polymeric adsorbent resin, chromatographically separating the decolorized chloroeremomycin using a hydrophobic polymeric resin column, and precipitating the separated chloroeremomycin using an organic solvent,
d) preparing a solution of the precipitated chloroeremomycin of c) and a copper salt in an organic solvent, reacting the solution with 4-chloro-4'-biphenyl carboxaldehyde, and precipitating oritavancin-copper complex from the solution using acetonitrile,
e) de-complexing copper from the oritavancin-copper complex of d) by adding a aqueous acid and separating the de-complexed oritavancin using a polymeric hydrophobic resin, wherein the adding and separating are performed concurrently or sequentially,
f) concentrating the oritavancin solution eluted from the resin in e),
g) precipitating oritavancin from the concentrate of f) in aqueous ethanol, and
h) drying the precipitated oritavancin.

In certain aspects of the first through third embodiments, the oritavancin drug substance preparation has a maximum impurity level of not more than 1.6% by peak area of impurity 1 and impurity 7.

In certain aspects of the first through third embodiments, the oritavancin drug substance preparation has a maximum impurity level of not more than 1.5% by peak area of impurity 1 and 0.6% by peak area of impurity 7.

In certain aspects of the first through third embodiments, the purity level of the oritavancin drug substance preparation is measured by HPLC. In particular aspects, the purity level is measured by HPLC, wherein the HPLC method includes a C18 reverse-phase stationary phase and a gradient of mobile phase B, which is phosphoric acid/water/acetonitrile/tetrahydrofuran at a ratio of about 1/1000/1500/25 (v/v/v/v), in mobile phase A, which is phosphoric acid/water/tetrahydrofuran at a ratio of about 1/1000/10 (v/v/v).

In certain aspects of the second and third embodiments, the chloroeremomycin-producing microorganism is a species of microorganism selected from one of the following genera: *Nocardia, Amycolatopsis* and *Kibdelosporangium*. In a particular aspect, the chloroeremomycin-producing microorganism is *Kibdelosporangium aridum*.

In certain aspects of the first embodiment, nitrogen atoms of the drug substance preparation are derived from a non-animal source.

In a fourth embodiment, the invention is directed to an oritavancin drug substance preparation of oritavancin, or a salt thereof, having about 90% purity or greater by peak area relative to impurities 1-16, defined by peak A of FIG. 1 and peaks B-P of FIG. 2, respectively.

In a fifth embodiment the invention is directed to a method for preparing an oritavancin drug substance preparation of oritavancin, or a salt thereof, having about 90% purity or greater by peak area relative to impurities 1-16, defined by peak A of FIG. 1 and peaks B-P of FIG. 2, respectively, comprising the steps of:
a) growing a culture of a chloroeremomycin-producing microorganism under fermentative conditions in a medium free of animal-sourced material (ASM) and under conditions promoting biosynthesis of chloroeremomycin by the culture,
b) recovering chloroeremomycin from fermentation broth of a) using a polymeric exchange resin,
c) decolorizing the chloroeremomycin recovered in b) using a polymeric adsorbent resin, chromatographically separating the decolorized chloroeremomycin using a hydrophobic polymeric resin column, and precipitating the separated chloroeremomycin using an organic solvent,
d) preparing a solution of the precipitated chloroeremomycin of c) and a copper salt in an organic solvent, reacting the solution with 4-chloro-4'-biphenyl carboxaldehyde, and precipitating oritavancin-copper complex from the solution using acetonitrile,
e) de-complexing copper from the oritavancin-copper complex of d) by adding a aqueous acid and separating the de-complexed oritavancin using a polymeric hydrophobic resin, wherein the adding and separating are performed concurrently or sequentially,
f) concentrating the oritavancin solution eluted from the resin in e),
g) precipitating oritavancin from the concentrate of f) in aqueous ethanol, and
h) drying the precipitated oritavancin, thereby preparing a preparing an oritavancin drug substance preparation of oritavancin, or a salt thereof, having about 90% purity or greater by peak area relative to impurities 1-16, defined by peak A of FIG. 1 and peaks B-P of FIG. 2, respectively.

In a sixth embodiment the invention is directed to an oritavancin drug substance preparation of oritavancin, or a salt thereof, having about 90% purity or greater by peak area relative to impurities 1-16, defined by peak A of FIG. 1 and peaks B-P of FIG. 2, respectively, prepared by a method comprising the steps of:
a) growing a culture of a chloroeremomycin-producing microorganism under fermentative conditions in a medium free of animal-sourced material (ASM) and under conditions promoting biosynthesis of chloroeremomycin by the culture,
b) recovering chloroeremomycin from fermentation broth of a) using a polymeric exchange resin,
c) decolorizing the chloroeremomycin recovered in b) using a polymeric adsorbent resin, chromatographically separating the decolorized chloroeremomycin using a hydrophobic polymeric resin column, and precipitating the separated chloroeremomycin using an organic solvent,
d) preparing a solution of the precipitated chloroeremomycin of c) and a copper salt in an organic solvent, reacting the solution with 4-chloro-4'-biphenyl carboxaldehyde, and precipitating oritavancin-copper complex from the solution using acetonitrile,
e) de-complexing copper from the oritavancin-copper complex of d) by adding a aqueous acid and separating the de-complexed oritavancin using a polymeric hydrophobic resin, wherein the adding and separating are performed concurrently or sequentially, concentrating the oritavancin solution eluted from the resin in e), g) precipitating oritavancin from the concentrate of f) in aqueous ethanol, and h) drying the precipitated oritavancin.

In certain aspects of the fourth through sixth embodiments, the purity level of the oritavancin drug substance preparation is about 96% purity or greater.

In certain aspects of the fourth through sixth embodiments, the purity level of the oritavancin drug substance preparation is between about 90 and 96% purity.

In certain aspects of the fourth through sixth embodiments, the purity level of the oritavancin drug substance preparation is measured by HPLC. In particular aspects, the purity level is measured by HPLC, wherein the HPLC method includes a C18 reverse-phase stationary phase and a gradient of mobile phase B, which is phosphoric acid/water/acetonitrile/tetrahydrofuran at a ratio of about 1/1000/1500/25 (v/v/v/v), in mobile phase A, which is phosphoric acid/water/tetrahydrofuran at a ratio of about 1/1000/10 (v/v/v).

In certain aspects of the fifth and sixth embodiments, the chloroeremomycin-producing microorganism is a species of microorganism selected from one of the following genera: *Nocardia, Amycolatopsis* and *Kibdelosporangium*. In a particular aspect, the chloroeremomycin-producing microorganism is *Kibdelosporangium aridum*.

In certain aspects of the fourth embodiment, nitrogen atoms of the drug substance preparation are derived from a non-animal source.

In a seventh embodiment, the invention is directed to an oritavancin drug substance preparation of oritavancin, or a salt thereof, having about 90% purity or greater.

In an eighth embodiment the invention is directed to a method for preparing an oritavancin drug substance preparation of oritavancin, or a salt thereof, having about 90% purity or greater, comprising the steps of:

a) growing a culture of a chloroeremomycin-producing microorganism under fermentative conditions in a medium free of animal-sourced material (ASM) and under conditions promoting biosynthesis of chloroeremomycin by the culture, b) recovering chloroeremomycin from fermentation broth of a) using a polymeric exchange resin, c) decolorizing the chloroeremomycin recovered in b) using a polymeric adsorbent resin, chromatographically separating the decolorized chloroeremomycin using a hydrophobic polymeric resin column, and precipitating the separated chloroeremomycin using an organic solvent, d) preparing a solution of the precipitated chloroeremomycin of c) and a copper salt in an organic solvent, reacting the solution with 4-chloro-4'-biphenyl carboxaldehyde, and precipitating oritavancin-copper complex from the solution using acetonitrile, e) de-complexing copper from the oritavancin-copper complex of d) by adding a aqueous acid and separating the de-complexed oritavancin using a polymeric hydrophobic resin, wherein the adding and separating are performed concurrently or sequentially, f) concentrating the oritavancin solution eluted from the resin in e), g) precipitating oritavancin from the concentrate of f) in aqueous ethanol, and h) drying the precipitated oritavancin, thereby preparing an oritavancin drug substance preparation of oritavancin, or a salt thereof, having about 90% purity or greater.

In a ninth embodiment the invention is directed to an oritavancin drug substance preparation of oritavancin, or a salt thereof, having about 90% purity or greater, prepared by a method comprising the steps of:

a) growing a culture of a chloroeremomycin-producing microorganism under fermentative conditions in a medium free of animal-sourced material (ASM) and under conditions promoting biosynthesis of chloroeremomycin by the culture, b) recovering chloroeremomycin from fermentation broth of a) using a polymeric exchange resin, c) decolorizing the chloroeremomycin recovered in b) using a polymeric adsorbent resin, chromatographically separating the decolorized chloroeremomycin using a hydrophobic polymeric resin column, and precipitating the separated chloroeremomycin using an organic solvent, d) preparing a solution of the precipitated chloroeremomycin of c) and a copper salt in an organic solvent, reacting the solution with 4-chloro-4'-biphenyl carboxaldehyde, and precipitating oritavancin-copper complex from the solution using acetonitrile, e) de-complexing copper from the oritavancin-copper complex of d) by adding a aqueous acid and separating the de-complexed oritavancin using a polymeric hydrophobic resin, wherein the adding and separating are performed concurrently or sequentially, f) concentrating the oritavancin solution eluted from the resin in e), g) precipitating oritavancin from the concentrate of f) in aqueous ethanol, and h) drying the precipitated oritavancin.

In certain aspects of the seventh through ninth embodiments, the purity level of the oritavancin drug substance preparation is about 96% purity or greater.

In certain aspects of the seventh through ninth embodiments, the purity level of the oritavancin drug substance preparation is between about 90 and 96% purity.

In certain aspects of the seventh through ninth embodiments, the purity level of the oritavancin drug substance preparation is measured by HPLC. In particular aspects, the purity level is measured by HPLC, wherein the HPLC method includes a C18 reverse-phase stationary phase and a gradient of mobile phase B, which is phosphoric acid/water/acetonitrile/tetrahydrofuran at a ratio of about 1/1000/1500/25 (v/v/v/v), in mobile phase A, which is phosphoric acid/water/tetrahydrofuran at a ratio of about 1/1000/10 (v/v/v).

In certain aspects of the eighth and ninth embodiments, the chloroeremomycin-producing microorganism is a species of microorganism selected from one of the following genera: *Nocardia, Amycolatopsis* and *Kibdelosporangium*. In a particular aspect, the chloroeremomycin-producing microorganism is *Kibdelosporangium aridum*.

In certain aspects of the seventh embodiment, nitrogen atoms of the drug substance preparation are derived from a non-animal source.

In a tenth embodiment the invention is directed to a pharmaceutical composition comprising an oritavancin drug substance preparation of the present invention and one or more pharmaceutically acceptable excipients, wherein the oritavancin drug substance preparation has a maximum impurity level of not more than 4.8% by peak area of impurity 2 (DEV A) and impurity 10 (oritavancin CR), defined by peaks B and J shown in FIG. 2, respectively.

In an eleventh embodiment the invention is directed to a method for preparing a pharmaceutical composition comprising an oritavancin drug substance preparation of the present invention and one or more pharmaceutically acceptable excipients, wherein the oritavancin drug substance preparation has a maximum impurity level of not more than 4.8% by peak area of impurity 2 and impurity 10, defined by peaks B and J of FIG. 2, respectively, comprising the steps of:

a) dissolving one or more pharmaceutically acceptable excipients in water having a pH of 2.5 to 3.5 to form a solution, b) dissolving oritavancin drug substance preparation in the solution of a) and adjusting the pH of the solution to 3.5 to 4.0, c) filtering the solution of b), and d) lyophilizing the filtered solution of c), thereby preparing a pharmaceutical composition comprising an oritavancin drug substance preparation and one or more pharmaceutically acceptable excipients, wherein the oritavancin drug substance preparation has a maximum impurity level of not more than 4.8% by peak area of impurity 2 and impurity 10, defined by peaks B and J of FIG. 2, respectively.

In a twelfth embodiment the invention is directed to a pharmaceutical composition comprising an oritavancin drug substance preparation of the present invention and one or more pharmaceutically acceptable excipients, wherein the oritavancin drug substance preparation has a maximum impurity level of not more than 4.8% by peak area of impurity 2 and impurity 10, defined by peaks B and J of FIG. 2, respectively, prepared by a method comprising the steps of:

a) dissolving one or more pharmaceutically acceptable excipients in water having a pH of 2.5 to 3.5 to form a solution, b) dissolving oritavancin drug substance preparation in the solution of a) and adjusting the pH of the solution to 3.5 to 4.0, c) filtering the solution of b), and d) lyophilizing the filtered solution of c).

In certain aspects of the tenth through twelfth embodiments, the oritavancin drug substance preparation has a maximum impurity level of not more than 3.0% by peak area of impurity 2 and impurity 10.

In certain aspects of the tenth through twelfth embodiments, the oritavancin drug substance preparation has a maximum impurity level of not more than 1.9% by peak area of impurity 2 and 2.9% by peak area of impurity 10.

In certain aspects of the tenth through twelfth embodiments, the purity level of the oritavancin drug substance preparation in the pharmaceutical composition is measured by HPLC. In particular aspects, the purity level of the oritavancin drug substance preparation in the pharmaceutical composition is measured by HPLC, wherein the HPLC method includes a C18 reverse-phase stationary phase and a gradient of mobile phase B, which is phosphoric acid/water/acetonitrile/tetrahydrofuran at a ratio of about 1/1000/1500/25 (v/v/v/v), in mobile phase A, which is phosphoric acid/water/tetrahydrofuran at a ratio of about 1/1000/10 (v/v/v).

In certain aspects of the eleventh and twelfth embodiments, the filtered solution of c) is added to a sterilized vial prior to the lyophilizing of d).

In certain aspects of the eleventh and twelfth embodiments, the pH is adjusted in b) to 3.6 to 3.8.

In certain aspects of the eleventh and twelfth embodiments, the lyophilizing achieves a level of moisture of less than about 5% by weight.

In certain aspects of the tenth through twelfth embodiments, the one or more pharmaceutically acceptable excipients are selected from the group consisting of mannitol, sorbitol, sucrose and trehalose.

In certain aspects of the tenth through twelfth embodiments, the pharmaceutically acceptable excipient is mannitol.

In certain aspects of the tenth through twelfth embodiments, the ratio of the drug substance preparation to the one or more excipients is 2:1 by weight.

In certain aspects of the tenth through twelfth embodiments, the pharmaceutical composition comprises about 56-68% of oritavancin drug substance preparation and about 44-32% of the one or more pharmaceutically acceptable excipients, by weight of the pharmaceutical composition.

In a thirteenth embodiment the invention is directed to a pharmaceutical composition comprising an oritavancin drug substance preparation of the present invention and one or more pharmaceutically acceptable excipients, wherein the oritavancin drug substance preparation has about 90% purity or greater by peak area relative to impurities 2-16, defined by peaks B-P of FIG. 2, respectively.

In a fourteenth embodiment the invention is directed to a method for preparing a pharmaceutical composition comprising an oritavancin drug substance preparation of the present invention and one or more pharmaceutically acceptable excipients, wherein the oritavancin drug substance preparation has about 90% purity or greater by peak area relative to impurities 2-16, defined by peaks B-P of FIG. 2, respectively, comprising the steps of:

a) dissolving one or more pharmaceutically acceptable excipients in water having a pH of 2.5 to 3.5 to form a solution, b) dissolving oritavancin drug substance preparation in the solution of a) and adjusting the pH of the solution to 3.5 to 4.0, c) filtering the solution of b), and d) lyophilizing the filtered solution of c), thereby preparing a pharmaceutical composition comprising an oritavancin drug substance preparation and one or more pharmaceutically acceptable excipients wherein the oritavancin drug substance preparation has about 90% purity or greater by peak area relative to impurities 2-16, defined by peaks B-P of FIG. 2, respectively.

In a fifteenth embodiment the invention is directed to a pharmaceutical composition comprising an oritavancin drug substance preparation of the present invention and one or more pharmaceutically acceptable excipients, wherein the oritavancin drug substance preparation has about 90% purity or greater by peak area relative to impurities 2-16, defined by peaks B-P of FIG. 2, respectively, prepared by a method comprising the steps of:

a) dissolving one or more pharmaceutically acceptable excipients in water having a pH of 2.5 to 3.5 to form a solution, b) dissolving oritavancin drug substance preparation in the solution of a) and adjusting the pH of the solution to 3.5 to 4.0, c) filtering the solution of b), and d) lyophilizing the filtered solution of c).

In certain aspects of the thirteenth through fifteenth embodiments, the purity level of the oritavancin drug substance preparation is about 96% purity or greater.

In certain aspects of the thirteenth through fifteenth embodiments, the purity level of the oritavancin drug substance preparation is between about 90 and 96% purity In certain aspects of the thirteenth through fifteenth embodiments, the purity level of the oritavancin drug substance preparation in the pharmaceutical composition is measured by HPLC. In particular aspects, the purity level of the oritavancin drug substance preparation in the pharmaceutical composition is measured by HPLC, wherein the HPLC method includes a C18 reverse-phase stationary phase and a gradient of mobile phase B, which is phosphoric acid/water/acetonitrile/tetrahydrofuran at a ratio of about 1/1000/1500/25 (v/v/v/v), in mobile phase A, which is phosphoric acid/water/tetrahydrofuran at a ratio of about 1/1000/10 (v/v/v).

In certain aspects of the fourteenth and fifteenth embodiments, the filtered solution of c) is added to a sterilized vial prior to the lyophilizing of d).

In certain aspects of the fourteenth and fifteenth embodiments, the pH is adjusted in b) to 3.6 to 3.8.

In certain aspects of the fourteenth and fifteenth embodiments, the lyophilizing achieves a level of moisture of less than about 5% by weight.

In certain aspects of the fourteenth and fifteenth embodiments, the one or more pharmaceutically acceptable excipients are selected from the group consisting of mannitol, sorbitol, sucrose and trehalose.

In certain aspects of the fourteenth and fifteenth embodiments, the pharmaceutically acceptable excipient is mannitol.

In certain aspects of the thirteenth through fifteenth embodiments, the ratio of the drug substance preparation to the one or more excipients is 2:1 by weight.

In certain aspects of the thirteenth through fifteenth embodiments, the pharmaceutical composition comprises about 56-68% of oritavancin drug substance preparation and about 44-32% of the one or more pharmaceutically acceptable excipients, by weight of the pharmaceutical composition.

In a sixteenth embodiment the invention is directed to a drug product or dosage form comprising a pharmaceutical composition of the present invention and one or more additional pharmaceutically acceptable excipients, wherein the oritavancin drug substance preparation has about 90% purity or greater by peak area relative to impurities 2-16, defined by peaks B-P of FIG. 2, respectively.

In a seventeenth embodiment the invention is directed to a method for preparing a drug product or dosage form comprising a pharmaceutical composition of the present invention and one or more additional pharmaceutically acceptable excipients, wherein the oritavancin drug substance preparation has about 90% purity or greater by peak area relative to impurities 2-16, defined by peaks B-P of FIG. 2, respectively, comprising dissolving a pharmaceutical composition of the present invention in Water for Injection or 5% dextrose in water to form a solution, wherein the concentration of oritavancin in the solution is from about 5 to about 30 mg/mL, thereby preparing a drug product or dosage form comprising a pharmaceutical composition of the present invention.

In an eighteenth embodiment the invention is directed to a drug product or dosage form comprising a pharmaceutical composition of the present invention and one or more additional excipients, wherein the oritavancin drug substance preparation has about 90% purity or greater by peak area relative to impurities 2-16, defined by peaks B-P of FIG. 2, respectively, prepared by a method comprising dissolving a pharmaceutical composition of the present invention in Water for Injection or 5% dextrose in water to form a solution, wherein the concentration of oritavancin in the solution is from about 5 to about 30 mg/mL.

In certain aspects of the sixteenth through eighteenth embodiments, the drug product or dosage form is an intravenous solution comprising 5% dextrose in water.

In certain aspects of the sixteenth through eighteenth embodiments, the purity level of the oritavancin drug substance preparation in drug product is measured by HPLC. In particular aspects, the purity level of the oritavancin drug substance preparation in the drug product is measured by HPLC, wherein the HPLC method includes a C18 reverse-phase stationary phase and a gradient of mobile phase B, which is phosphoric acid/water/acetonitrile/tetrahydrofuran at a ratio of about 1/1000/1500/25 (v/v/v/v), in mobile phase A, which is phosphoric acid/water/tetrahydrofuran at a ratio of about 1/1000/10 (v/v/v).

In a nineteenth embodiment the invention is directed to high purity chloroeremomycin, or a salt thereof, having a maximum impurity level of not more than 18.0% by peak area of impurities nucleus factors A, C and D, and substances P, Q, R, and S, defined by peaks 3, 1, 7, 2, 4, 5 and 6 of FIG. 3, respectively.

In a twentieth embodiment the invention is directed to a method for preparing high purity chloroeremomycin, or a salt thereof, having a maximum impurity level of not more than 18.0% by peak area of impurities nucleus factors A, C and D, and substances P, Q, R, and S, defined by peaks 3, 1, 7, 2, 4, 5 and 6 of FIG. 3, respectively, comprising the steps of:

a) growing a culture of a chloroeremomycin-producing microorganism under fermentative conditions in a medium free of animal-sourced material (ASM) and under conditions promoting biosynthesis of chloroeremomycin by the culture, b) recovering chloroeremomycin from fermentation broth of a) using a polymeric exchange resin, c) decolorizing the chloroeremomycin recovered in b) using a polymeric adsorbent resin, chromatographically separating the decolorized chloroeremomycin using a hydrophobic polymeric resin column, and precipitating the separated chloroeremomycin using an organic solvent, and d) drying the chloroeremomycin crystals, thereby preparing high purity chloroeremomycin or a salt thereof having a maximum impurity level of not more than 18.0% by peak area of impurities nucleus factors A, C and D, and substances P, Q, R, and S, defined by peaks 3, 1, 7, 2, 4, 5 and 6 of FIG. 3, respectively.

In a twenty-first embodiment the invention is directed to high purity chloroeremomycin, or a salt thereof, having a maximum impurity level of not more than 18.0% by peak area of impurities nucleus factors A, C and D, and substances P, Q, R, and S, defined by peaks 3, 1, 7, 2, 4, 5 and 6 of FIG. 3, respectively, prepared by a method comprising a) growing a culture of a chloroeremomycin-producing microorganism under fermentative conditions in a medium free of animal-sourced material (ASM) and under conditions promoting biosynthesis of chloroeremomycin by the culture, b) recovering chloroeremomycin from fermentation broth of a) using a polymeric exchange resin, c) decolorizing the chloroeremomycin recovered in b) using a polymeric adsorbent resin, chromatographically separating the decolorized chloroeremomycin using a hydrophobic polymeric resin column, and precipitating the separated chloroeremomycin using an organic solvent, and d) drying the chloroeremomycin crystals.

In certain aspects of the nineteenth through twenty-first embodiments, the drug substance preparation has a maximum impurity level of not more than 15.0% by peak area of impurities nucleus factors A, C and D, and substances P, Q, R, and S, defined by peaks 3, 1, 7, 2, 4, 5 and 6 of FIG. 3.

In certain aspects of the twentieth and twenty-first embodiments, the purity level of the chloroeremomycin is measured by HPLC. In particular aspects, the purity level of the chloroeremomycin is measured by HPLC, wherein the HPLC method includes a phenyl derivatized reverse-phase stationary phase and a gradient of mobile phase B, which is acetonitrile/water/formic acid/triethylamine at a ratio of about 40/60/0.2/0.03 (v/v/v/v) in mobile phase A, which is water/formic acid/triethylamine at a ratio of about 100/0.2/0.03 (v/v/v).

In certain aspects of the twentieth and twenty-first embodiments, the chloroeremomycin-producing microorganism is a species of microorganism selected from one of the following genera: *Nocardia, Amycolatopsis* and *Kibdelosporangium*. In a particular aspect, the chloroeremomycin-producing microorganism is *Kibdelosporangium aridum*.

In certain aspects of the nineteenth embodiment, nitrogen atoms of the high purity chloroeremomycin are derived from a non-animal source.

In a twenty-second embodiment the invention is directed to high purity chloroeremomycin, or a salt thereof, having a purity of about 82% or greater.

In a twenty-third embodiment the invention is directed to a method for preparing high purity chloroeremomycin, or a salt thereof, having a purity of about 82% or greater, comprising the steps of:
a) growing a culture of a chloroeremomycin-producing microorganism under fermentative conditions in a medium free of animal-sourced material (ASM) and under conditions promoting biosynthesis of chloroeremomycin by the culture,
b) recovering chloroeremomycin from fermentation broth of a) using a polymeric exchange resin,
c) decolorizing the chloroeremomycin recovered in b) using a polymeric adsorbent resin, chromatographically separating the decolorized chloroeremomycin using a hydrophobic polymeric resin column, and precipitating the separated chloroeremomycin using an organic solvent, and
d) drying the chloroeremomycin crystals, thereby preparing high purity chloroeremomycin or a salt thereof having a purity of about 82% or greater.

In a twenty-fourth embodiment the invention is directed to high purity chloroeremomycin, or a salt thereof, having a purity of about 82% or greater, prepared by a method comprising the steps of:
a) growing a culture of a chloroeremomycin-producing microorganism under fermentative conditions in a medium free of animal-sourced material (ASM) and under conditions promoting biosynthesis of chloroeremomycin by the culture,
b) recovering chloroeremomycin from fermentation broth of a) using a polymeric exchange resin,
c) decolorizing the chloroeremomycin recovered in b) using a polymeric adsorbent resin, chromatographically separating the decolorized chloroeremomycin using a hydrophobic polymeric resin column, and precipitating the separated chloroeremomycin using an organic solvent, and
d) drying the chloroeremomycin crystals.

In certain aspects of the twenty-second through twenty-fourth embodiments, the purity level of the chloroeremomycin is about 90% or greater.

In certain aspects of the twenty-second through twenty-fourth embodiments, the purity level of the chloroeremomycin is between about 82 and 95%.

In certain aspects of the twenty-second through twenty-fourth embodiments, the purity level of the chloroeremomycin is measured by HPLC. In particular aspects, the purity level of the chloroeremomycin is measured by HPLC, wherein the HPLC method includes a phenyl derivatized reverse-phase stationary phase and a gradient of mobile phase B, which is acetonitrile/water/formic acid/triethylamine at a ratio of about 40/60/0.2/0.03 (v/v/v/v) in mobile phase A, which is water/formic acid/triethylamine at a ratio of about 100/0.2/0.03 (v/v/v).

In certain aspects of the twenty-third through twenty-fourth embodiments, the chloroeremomycin-producing microorganism is a species of microorganism selected from one of the following genera: *Nocardia, Amycolatopsis* and *Kibdelosporangium*. In a particular aspect, the chloroeremomycin-producing microorganism is *Kibdelosporangium aridum*.

In certain aspects of the twenty-second embodiment, nitrogen atoms of the high purity chloroeremomycin are derived from a non-animal source.

In a twenty-fifth embodiment the invention is directed to a vial containing a lyophilized powder comprising a pharmaceutical composition of the present invention.

In certain aspects of the twenty-fifth embodiment, the vial is stoppered under a chemically inert dry gas. In certain preferred aspects, the chemically inert dry gas is nitrogen or argon.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF DRAWINGS

FIG. 4 provides a flow diagram of the nucleus factor B diacetate salt manufacturing process.

FIG. 5 provides a flow diagram of the oritavancin drug substance preparation chemistry.

FIG. 6 provides a schematic process flow diagram of the manufacturing process.

DETAILED DESCRIPTION OF THE INVENTION

I. Definitions

Figure 1:
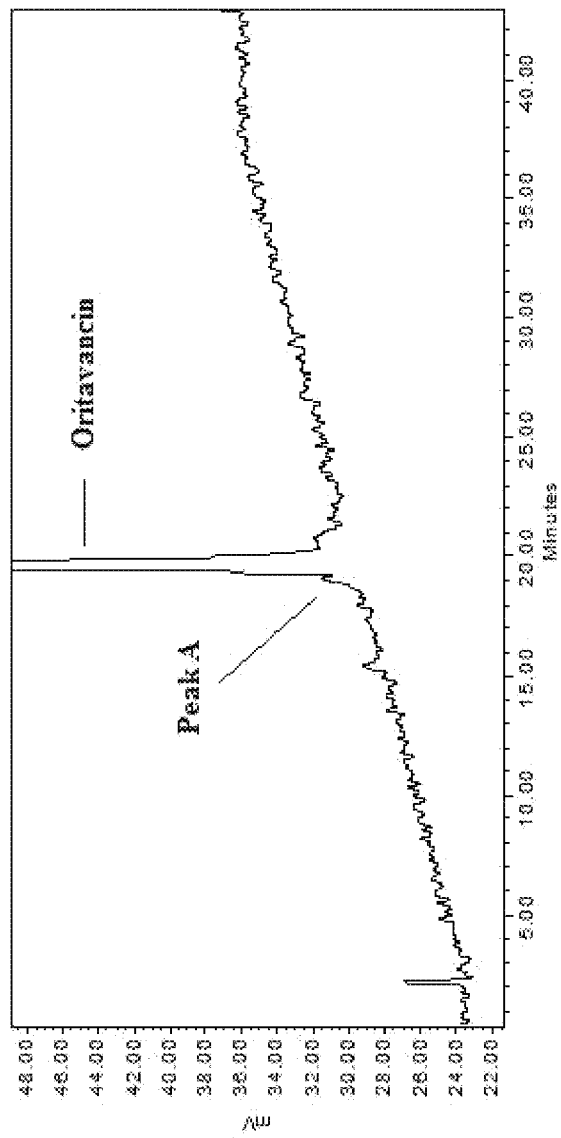
FIG. 1 is an HPLC chromatogram of an oritavacin drug substance preparation with a method that separates oritavancin factor A (peak A) from oritavancin.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, "treat" and all its forms and tenses (including, for example, treat, treating, treated, and treatment) refer to both therapeutic treatment and prophylactic or preventative treatment. Those in need of treatment include those already with a bacterial infection as well as those in which a bacterial infection is to be prevented.

As used herein, "drug substance preparation" or "active pharmaceutical ingredient" and all their forms and tenses refer to any substance or mixture of substances intended to be used in the manufacture of a pharmaceutical composition or a drug (medicinal) product and that, when used in the production of a pharmaceutical composition or a drug product, acts as the active ingredient of the pharmaceutical composition or drug product. Such substances are intended to furnish pharmacological activity or other direct effect in the diagnosis, cure, mitigation, treatment, or prevention of disease or to affect the structure and function of the body.

As used herein, "pharmaceutical composition" and all its forms and tenses refer to a formulation of (i) a drug substance preparation or active pharmaceutical ingredient, and (ii) one or more pharmaceutically acceptable excipients. Such formulations are generally the form of the drug substance preparation that is prepared by the manufacturer and shipped to a hospital pharmacy, for example. It is a stable form of the drug substance preparation that can be stored for days, weeks, months or years, that will typically be further mixed with one or more additional pharmaceutically acceptable excipients immediately before administration to a subject. Pharmaceutical compositions are often lyophilized formulations comprising a drug substance preparation and pharmaceutically acceptable excipients stored in sealed vials or ampoules.

As used herein, "drug product" or "dosage form" and all its forms and tenses refer to the drug substance preparation or active pharmaceutical ingredient in a formulation suitable for administration to a patient without further manipulation. Depending on the identity of the drug substance preparation, the drug product will be in one of two forms. It may either comprise (i) a drug substance preparation or active pharmaceutical ingredient, and (ii) one or more pharmaceutically acceptable excipients, or it may comprise (i) a pharmaceutical composition, and (ii) one or more additional pharmaceutically acceptable excipients.

II. The Present Invention

Oritavancin (I) is a novel, semi-synthetic glycopeptide antibiotic with activity against glycopeptide- (and in particular vancomycin-) resistant Gram positive microorganisms. Due to its rapid bactericidal activity (Belley et al., *Antimicrob. Agents Chemother.* 2010, 54, 5369), its complex mechanism of action (Zhanel et al., *Clin. Infect. Dis.* 2012, 54, S214), and its activity against planktonic and dormant microorganisms (WO 2009/126502), oritavancin is a promising agent in development for the treatment of serious bacterial infections which may or may not be associated with resistant microorganisms (Poulakou, G. and Giamarellou, H., *Expert Opin. Investig. Drugs* 2008, 17, 225; Karaoui et al., *Am. J. Health-Syst. Pharm.* 2013, 70, 23).

In particular, the pharmacokinetic and pharmacodynamic profile of oritavancin, associated with its concentration-dependent killing and a long half-life which allows for single dose treatment (U.S. Pat. No. 8,420,592), provides oritavancin with a marked potential for the treatment of many types of difficult infections.

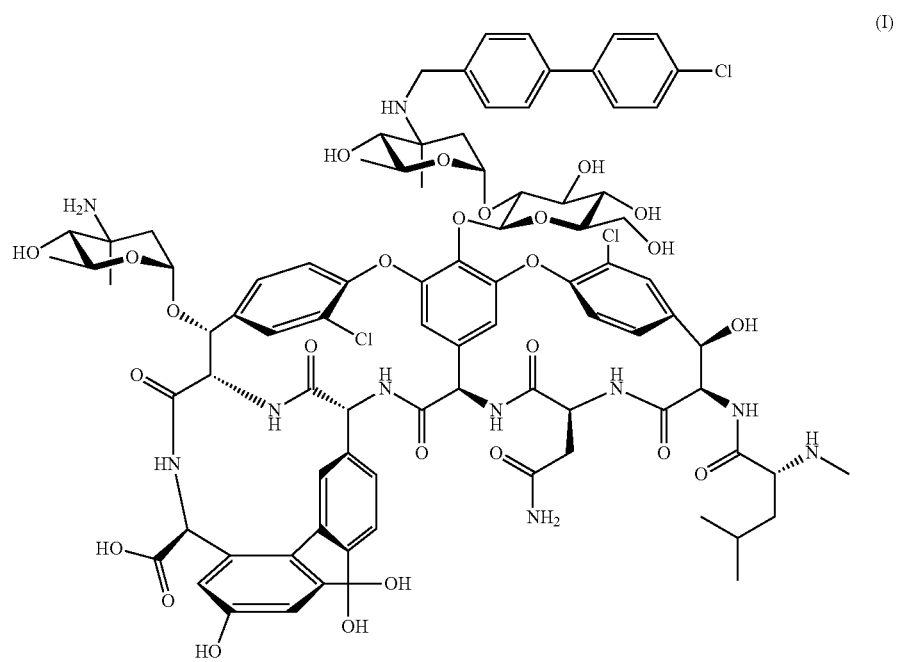

(I)

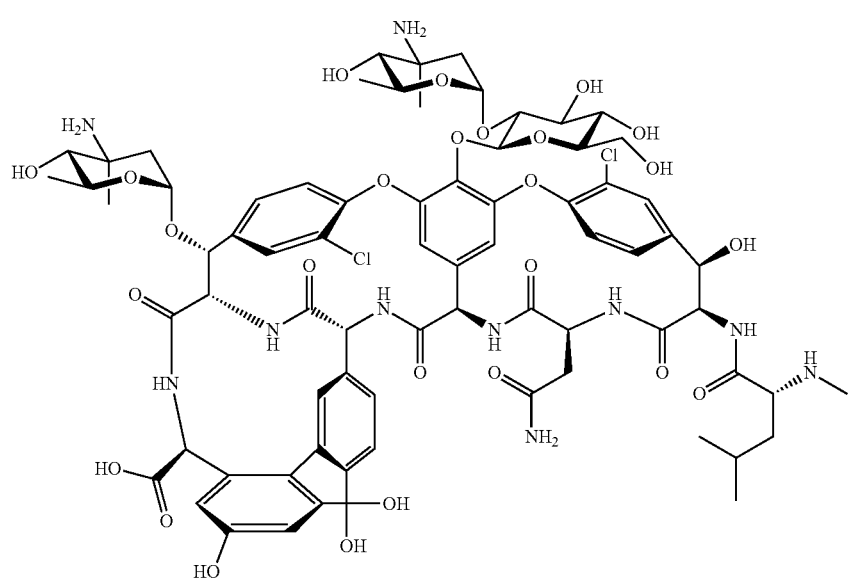

(II)

Oritavancin is manufactured in two main stages. In the first stage, the natural product chloroeremomycin (II; also termed "nucleus factor B" in some instances) is obtained biosynthetically via fermentation of a strain of *Kibdelosporangium aridum* (originally *Nocardia orientalis* in U.S. Pat. No. 5,312,738; U.S. Pat. No. 5,843,437; EP 265,071). In the second stage, a 4-(4-chlorophenyl)benzyl group is added to chloroeremomycin via reductive alkylation to furnish oritavancin (U.S. Pat. No. 5,952,466; U.S. Pat. No. 5,998,581; U.S. Pat. No. 5,939,382).

In both stages, the generation of the compound of interest is followed by lengthy isolation procedures, involving the chromatographic separation of chloroeremomycin from the fermentation medium (as exemplified by U.S. Pat. No. 4,845,194), and of oritavancin from the reaction mixture.

As expected, the biosynthetic processes producing chloroeremomycin also result in production of a number of chemically related impurities and in particular nucleus factor A (A82846A, eremomycin, III), nucleus factor C (A82846C, IV) and nucleus factor D (V). During reductive alkylation of chloroeremomycin to oritavancin, these impurities are likewise alkylated and converted to the impurities oritavancin factor A (VI), oritavancin factor C (VII) and oritavancin factor D (VIII).

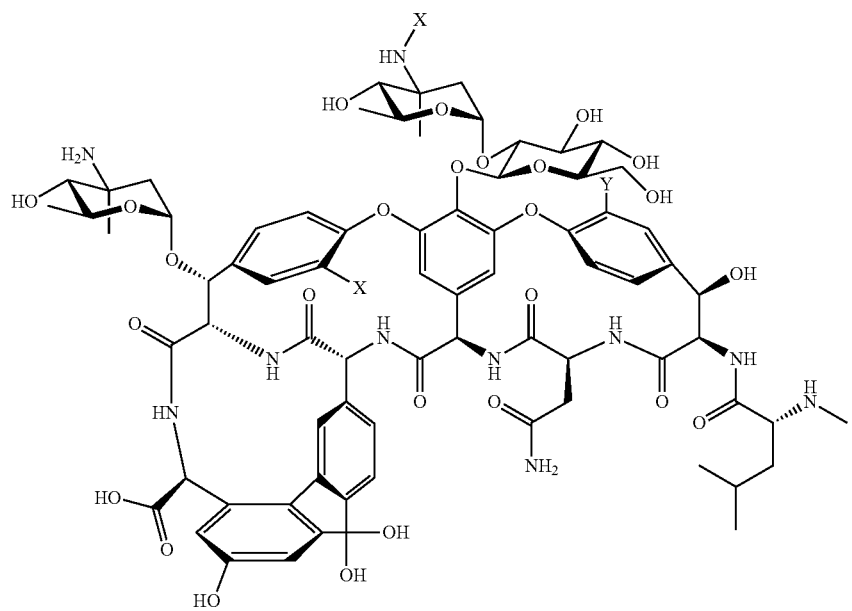

(III) X = H, Y = Cl, Z = H
(IV) X = H, Y = H, Z = H
(V) X = Cl, Y = Cl, Z = $CH_2CO_2H$

-continued

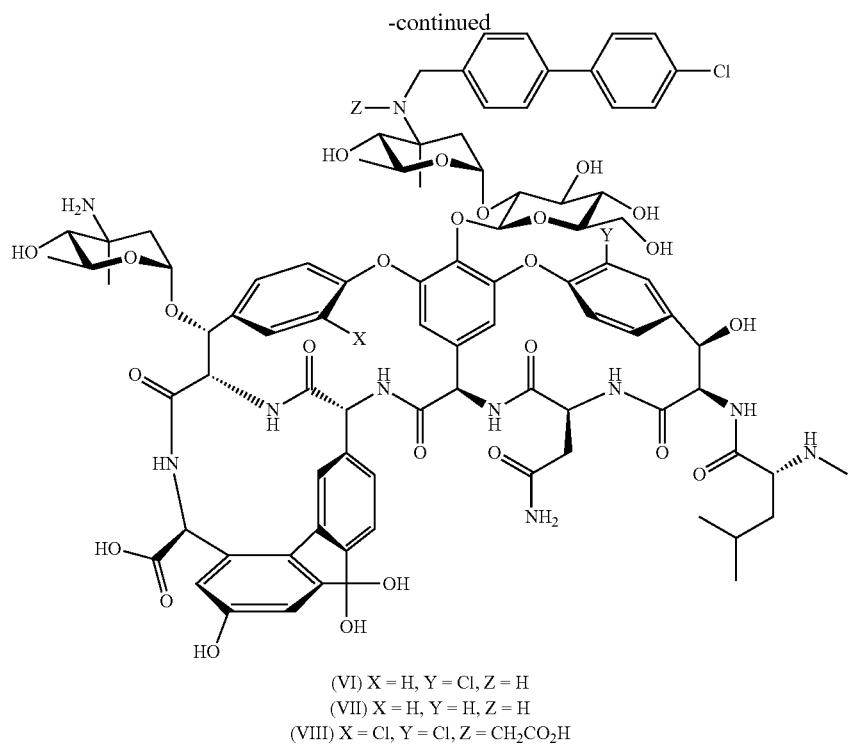

(VI) X = H, Y = Cl, Z = H
(VII) X = H, Y = H, Z = H
(VIII) X = Cl, Y = Cl, Z = CH$_2$CO$_2$H

Given the small differences between these impurities and the desired compounds (chloroeremomycin and oritavancin), any chromatographic separation, especially at commercial scales, would only be able to afford modest separation.

There are a number of additional, closely-related impurities associated with chloroeremomycin, including substances P, Q, R and S, which lack structural identification but closely coelute with chloroeremomycin. These lead to further unspecified impurities in oritavancin, of which there is a large number. In fact, in the chromatographic profile of oritavancin, 40 different peaks have been identified.

Given the chemically complex nature of oritavancin, there are also a number of impurities that can result from the handling of oritavancin itself, such as the process of preparing the drug product (i.e., pharmaceutical compositions comprising oritavancin and an excipient), and upon storage. These impurities may result from deglycosylation, amide bond hydrolysis, or configurational changes to the large number of structural elements in the molecule.

For some impurities, a limited amount of information regarding the antibacterial activity and safety of the impurity can be obtained. However, for obvious practical reasons specific information regarding activity cannot be determined for individual impurities for the thousands of bacterial strains encountered clinically and against which the drug itself (oritavancin) has been evaluated to establish spectrum (see for example: Arhin et al., *Antimicorb. Agents Chemother.* 2009, 53, 53). Similarly, while simple short toxicology studies may be possible for a few isolatable impurities, such studies cannot be performed for all the impurities and certainly not to the extent that oritavancin itself is evaluated to establish safety. As a result, controlling impurity levels in the drug product is the only means for ensuring safe and efficacious treatment of patients.

In light of the medical and therapeutic applications of oritavancin, and under circumstances where the impact of individual impurities on the safety and the efficacy of the drug is very difficult to ascertain, the present invention is directed to (i) drug substance preparations having low levels of impurities, (ii) methods for production of such drug substance preparations, (iii) pharmaceutical compositions comprising the drug substance preparations and one or more excipients, formulated to inhibit formation of impurities, (iv) methods for production of such pharmaceutical compositions, (v) drug products (pharmaceutical compositions in preparations intended for use in a patient without further manipulation) formulated to inhibit formation of impurities, and (vi) methods for production of such drug product, among other important embodiments of the invention.

To achieve each embodiment of the invention, the inventors have found it to be critical that the fermentation produces a very low level of impurities, ensuring that both chloroeremomycin and oritavancin meet adequate levels of purity for use as pharmaceuticals. The original fermentation media reported in U.S. Pat. No. 5,312,738, U.S. Pat. No. 5,843,437 and EP Patent No. 265071 for the production of chloroeremomycin involved the use of animal-sourced material (ASM) as sources of complex nitrogen during fermentation. After extensive research, the inventors surprisingly found that switching to a medium devoid of ASM leads to a higher purity chloroeremomycin and consequently to a higher purity oritavancin. This discovery allowed each of the embodiments of the invention described herein to be achieved.

Upon additional extensive research, the inventors found that under specific circumstances, oritavancin can be manipulated, formulated and stored to minimize the presence of impurities in the final pharmaceutical composition thus achieving aspects (iii) and (iv) of the invention. By producing drug products using the drug substance preparations and pharmaceutical compositions of the invention, aspects (v) and (vi) have also been achieved. Further, the high purity chloroeremomycin described herein was also achieved.

Drug Substance Preparation Comprising Oritavancin

The present invention includes drug substance preparations of oritavancin or a salt thereof (also termed "oritavancin drug substance preparations" herein), wherein a minimum level of purity (or a maximum level of impurity) has been achieved in the preparation. In one aspect of the invention, the level of purity/impurity of the oritavancin drug substance preparation is defined by the peak area of one or more selected impurities on an HPLC chromatogram. In a particular embodiment, the oritavancin drug substance preparation has a maximum impurity level of not more than 3.0% by peak area of impurity 1 (oritavancin factor A) and impurity 7 (oritavancin factor C), defined by peak A of FIG. 1 and peak G of FIG. 2, respectively. In alternative aspects, the maximum impurity level is not more than 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, or 0.1% by peak area of impurity 1 and impurity 7. In a particular aspect, the oritavancin drug substance preparation has a maximum impurity level of not more than 2.1% by peak area of impurity 1 and impurity 7. In another particular aspect, the oritavancin drug substance preparation has a maximum impurity level of not more than 1.6% by peak area of impurity 1 and impurity 7. The relative amounts of impurities 1 and 7 can vary and include not more than 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, or 0.1% of impurity 1 in the combined amount of impurities 1 and 7 in the drug substance preparation.

Figure 2:
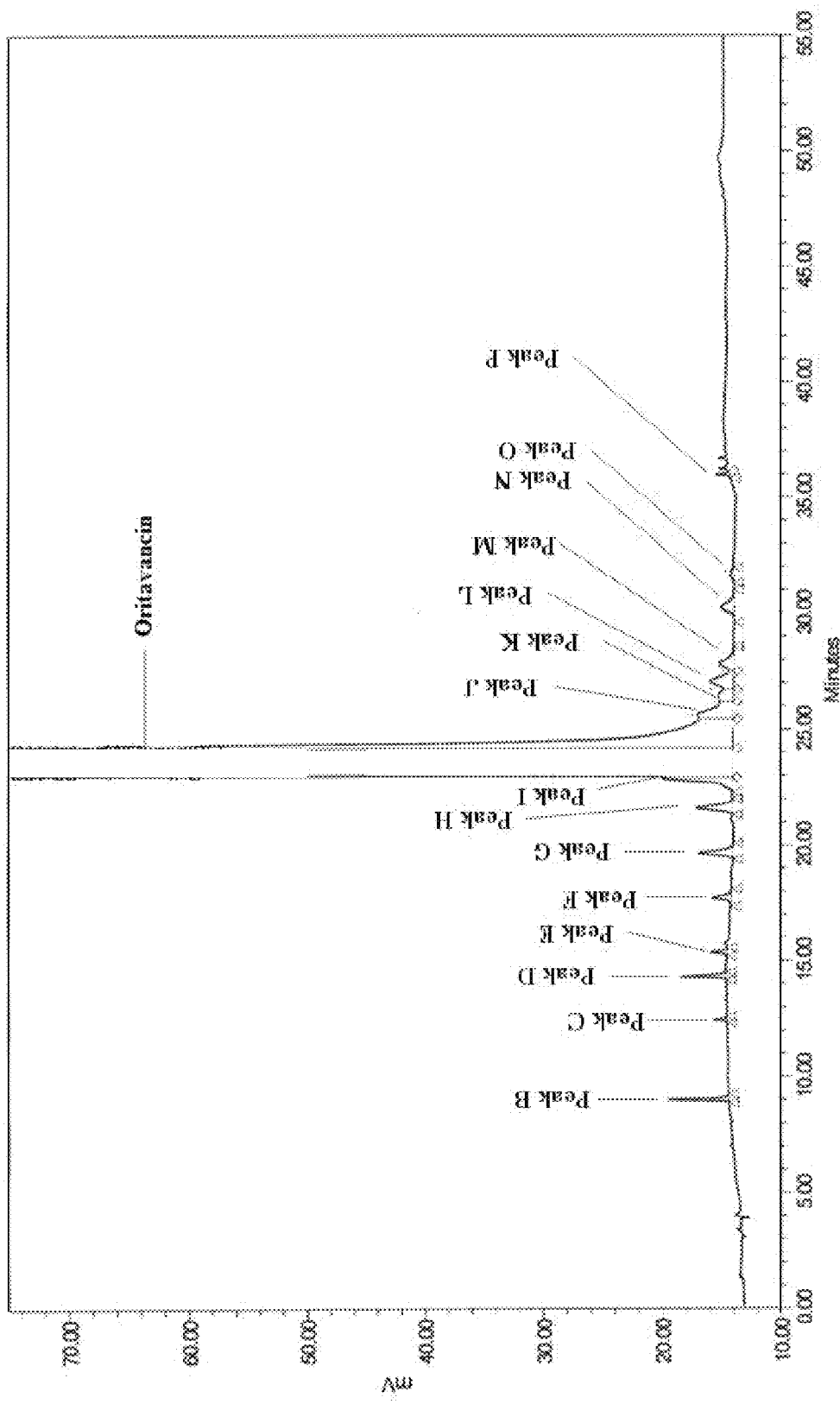
FIG. 2 is an HPLC chromatogram of an oritavacin drug substance preparation with a method that separates peaks B-P from oritavancin.

In another particular embodiment, the oritavancin drug substance preparation has about 85% purity or greater by peak area relative to impurities 1-16, defined by peak A of FIG. 1 and peaks B-P of FIG. 2, respectively. In alternative aspects, the preparation has a purity of about 86%, 87%, 88%, 89%, 90%, 91%, 92%, 93%, 94%, 95%, 96%, 97%, 98% or 99% or greater by peak area relative to impurities 1-16. In a particular aspect, the oritavancin drug substance preparation has about 90% purity or greater by peak area relative to impurities 1-16. In another particular aspect, the oritavancin drug substance preparation has a purity of between about 85 and 90%, between about 86 and 91%, between about 87 and 92%, between about 88 and 93%, between about 89 and 94%, between about 90 and 95%, between about 90 and 96%, between about 91 and 96%, or between about 92 and 97%, by peak area relative to impurities 1-16.

In another particular embodiment, the oritavancin drug substance preparation has about 85% purity or greater. In alternative aspects, the oritavancin drug substance preparation has a purity of about 86%, 87%, 88%, 89%, 90%, 91%, 92%, 93%, 94%, 95%, 96%, 97%, 98% or 99% or greater. In a particular aspect, the oritavancin drug substance preparation has about 90% purity or greater. In another particular aspect, the oritavancin drug substance preparation has a purity of between about 85 and 90%, between about 86 and 91%, between about 87 and 92%, between about 88 and 93%, between about 89 and 94%, between about 90 and 95%, between about 90 and 96%, between about 91 and 96%, or between about 92 and 97%.

Each of the oritavancin drug substance preparations of the present invention may be further characterized by its stability over time. In one aspect, the oritavancin drug substance preparations of the present invention exhibit less than a 1.0% increase by peak area in the level of impurities 2 and 10 within 48 months when stored refrigerated. In other aspects, the increase is less than a 0.1%, 0.2%, 0.3%, 0.4%, 0.6%, 0.7%, 0.8%, 0.9%, or 1.0% increase over 2, 4, 6, 8, 10, 12, 14, 16, 18, 20, 22, 24, 26, 28, 30, 32, 34, 36, 38, 40, 42, 44, 46, 48, 50, 52, 54, 56, 58, 60 or more months. In another aspect, the oritavancin drug substance preparations of the present invention exhibit less than a 1.5% increase by peak area in the level of impurities 1-16 within 48 months when stored refrigerated. In other aspects, the increase is less than a 0.1%, 0.2%, 0.3%, 0.4%, 0.6%, 0.7%, 0.8%, 0.9%, or 1.0% increase over 2, 4, 6, 8, 10, 12, 14, 16, 18, 20, 22, 24, 26, 28, 30, 32, 34, 36, 38, 40, 42, 44, 46, 48, 50, 52, 54, 56, 58, 60 or more months. In further aspect, the oritavancin drug substance preparations of the present invention exhibit less than a 1.5% increase in impurities within 48 months when stored refrigerated. In other aspects, the increase is less than a 0.1%, 0.2%, 0.3%, 0.4%, 0.6%, 0.7%, 0.8%, 0.9%, or 1.0% increase over 2, 4, 6, 8, 10, 12, 14, 16, 18, 20, 22, 24, 26, 28, 30, 32, 34, 36, 38, 40, 42, 44, 46, 48, 50, 52, 54, 56, 58, 60 or more months.

Methods for Preparing Drug Substance Preparations Comprising Oritavancin

The present invention also includes methods of preparing the drug substance preparations of oritavancin or a salt thereof, as defined herein, wherein a minimum level of purity (or a maximum level of impurity) has been achieved.

In a particular embodiment, the method of preparing an oritavancin drug substance preparation of the present invention comprising the steps of:

a) growing a culture of a chloroeremomycin-producing microorganism under fermentative conditions in a medium free of animal-sourced material (ASM) and under conditions promoting biosynthesis of chloroeremomycin by the culture, b) recovering chloroeremomycin from fermentation broth of a) using a polymeric exchange resin, c) decolorizing the chloroeremomycin recovered in b) using a polymeric adsorbent resin, chromatographically separating the decolorized chloroeremomycin using a hydrophobic polymeric resin column, and precipitating the separated chloroeremomycin using an organic solvent, d) preparing a solution of the precipitated chloroeremomycin of c) and a copper salt in an organic solvent, reacting the solution with 4-chloro-4'-biphenyl carboxaldehyde, and precipitating oritavancin-copper complex from the solution using acetonitrile, e) de-complexing copper from the oritavancin-copper complex of d) by adding a aqueous acid and separating the de-complexed oritavancin using a polymeric hydrophobic resin, wherein the adding and separating are performed concurrently or sequentially, f) concentrating the oritavancin solution eluted from the resin in e), g) precipitating oritavancin from the concentrate of f) in aqueous ethanol, and h) drying the precipitated oritavancin, thereby preparing a preparing an oritavancin drug substance preparation of the present invention. Such drug substance preparations include (i) a drug substance preparation of oritavancin, or a salt thereof, having a maximum impurity level of not more than 3.0% by peak area of impurity 1 (oritavancin factor A) and impurity 7 (oritavancin factor C), defined by peak A of FIG. 1 and peak G of FIG. 2, respectively; (ii) a drug substance preparation of oritavancin, or a salt thereof, having about 85% purity or greater by peak area relative to impurities 1-16, defined by peak A of FIG. 1 and peaks B-P of FIG. 2, respectively; and (iii) a drug substance preparation of oritavancin, or a salt thereof, having about 85% purity or greater.

In the method for preparing an oritavancin drug substance preparation described above, the chloroeremomycin-producing microorganism may be any microorganism that innately produces chloroeremomycin or that is engineered to produce chloroeremomycin. Suitable microorganisms include, but are not limited to, one or more microorganisms of the following genera: *Nocardia, Amycolatopsis* and *Kibdelosporangium*. In a particular aspect, the chloroeremomycin-producing microorganism is *Kibdelosporangium aridum*.

The fermentative conditions of step (a) generally involve the use of sources of carbohydrates, nitrogen, oligoelements, cations and phosphate at 30-35° C.

The medium free of animal-sourced material (ASM) is media that is supplemented with a nitrogen source that is not derived from animal. Suitable sources of nitrogen that may be used in the media include, but are not limited to, enzymatic digests of soybean meal/flour. The critical factor is that it serves as a source of organic nitrogen. Suitable media includes, but is not limited to, aqueous solutions of magnesium, calcium, potassium, phosphate and primary grown yeast.

Conditions promoting biosynthesis of chloroeremomycin by the culture include, but are not limited to, a temperature range of 20-40° C. and aeration and agitation rates that are sufficient to maintain growth of the microorganism.

Suitable polymeric exchange resins for use in recovering chloroeremomycin from the fermentation broth include, but are not limited to, sulfonated macroporous copolymers of styrene and divinylbenzene.

Suitable polymeric adsorbent resins for use in decolorizing the chloroeremomycin recovered include, but are not limited to, non-functionalized macroporous copolymers of styrene and divinylbenzene.

Suitable hydrophobic polymeric resin columns for use in chromatographically separating the decolorized chloroeremomycin include, but are not limited to, non-functionalized macroporous copolymers of styrene and divinylbenzene.

Suitable organic solvents for use in precipitating the separated chloroeremomycin include, but are not limited to, methanol.

Suitable organic solvents for use preparing a solution of the precipitated chloroeremomycin of and a copper salt in include, but are not limited to, methanol.

Suitable aqueous acids for use in de-complexing copper from the oritavancin-copper complex include, but are not limited to, formic acid and phosphoric acid.

Suitable polymeric hydrophobic resins for use in separating the de-complexed oritavancin include, but are not limited to, non-functionalized macroporous copolymers of styrene and divinylbenzene.

Suitable means for concentrating the oritavancin solution eluted from the resin include, but are not limited to, distillation of volatile solvents under reduced pressure or ultrafiltration/diafiltration.

Suitable means for drying the precipitated oritavancin include, but are not limited to, drying on a tray or in a Nutsche filter at elevated temperature and reduced pressure.

The method for preparing an oritavancin drug substance preparation may include some additional optional steps. For example, a concentrating step and a precipitating step may be performed after the decolorization and prior to the chromatography. The concentrating step may be performed by distillation of the volatile solvents under reduced pressure. The precipitating step may be performed by adjustment of the solution to an alkaline pH. In addition, a concentrating step may be performed after chromatography and prior to precipitation. This concentrating step may be performed by distillation of the volatile solvents under reduced pressure. Further, the decolorized chloroeremomycin may be chromatographically separated on reverse phase silica gel rather than using a hydrophobic polymeric resin column. Moreover, the reaction of a solution comprising chloroeremomycin and a copper salt with 4-chloro-4'-biphenyl carboxaldehyde may be terminated using a hydride reagent. Finally, the de-complexing of copper from the oritavancin-copper complex is an optional step as the step of separating the de-complexed oritavancin on a polymeric hydrophobic resin will also serve to remove the copper from the oritavancin.

The present invention also encompasses oritavancin drug substance preparations prepared by the methods provided herein.

Pharmaceutical Compositions Comprising Oritavancin Drug Substance Preparations

The present invention includes pharmaceutical compositions comprising an oritavancin drug substance preparation of the present invention (i.e., a drug substance preparation of oritavancin, or a salt thereof, wherein a minimum level of purity (or a maximum level of impurity) has been achieved) and one or more pharmaceutically acceptable excipients. In one aspect of the invention, the level of purity/impurity of the oritavancin drug substance preparation is defined by the peak area of one or more selected impurities on an HPLC chromatogram. In a particular embodiment, the pharmaceutical composition comprises an oritavancin drug substance preparation and one or more pharmaceutically acceptable excipients, wherein the oritavancin drug substance preparation has a maximum impurity level of not more than 5.5% by peak area of impurity 2 (DEV A) and impurity 10 (oritavancin CR), defined by peaks B and J shown in FIG. 2, respectively. In alternative aspects, the maximum impurity level is not more than 5.4%, 5.3%, 5.2%, 5.1%, 5.0%, 4.9%, 4.8%, 4.7%, 4.6%, 4.5%, 4.4%, 4.3%, 4.2%, 4.1%, 4.0%, 3.9%, 3.8%, 3.7%, 3.6%, 3.5%, 3.4%, 3.3%, 3.2%, 3.1%, 3.0%, 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, or 0.1% by peak area of impurity 2 and impurity 10. In a particular aspect, the oritavancin drug substance preparation has a maximum impurity level of not more than 4.8% by peak area of impurity 2 and impurity 10. In another particular aspect, the oritavancin drug substance preparation has a maximum impurity level of not more than 3.0% by peak area of impurity 2 and impurity 10. The relative amounts of impurities 2 and 10 can vary and include not more than 5.4%, 5.3%, 5.2%, 5.1%, 5.0%, 4.9%, 4.8%, 4.7%, 4.6%, 4.5%, 4.4%, 4.3%, 4.2%, 4.1%, 4.0%, 3.9%, 3.8%, 3.7%, 3.6%, 3.5%, 3.4%, 3.3%, 3.2%, 3.1%, 3.0%, 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, or 0.1% of impurity 2 in the combined amount of impurities 2 and 10 in the drug substance preparation.

In another particular embodiment, the pharmaceutical composition comprises an oritavancin drug substance preparation and one or more pharmaceutically acceptable excipients, in which the oritavancin drug substance preparation has about 85% purity or greater by peak area relative to impurities 2-16, defined by peaks B-P of FIG. 2, respectively. In alternative aspects, the oritavancin drug substance preparation has a purity of about 86%, 87%, 88%, 89%, 90%, 91%, 92%, 93%, 94%, 95%, 96%, 97%, 98% or 99% or greater by peak area relative to impurities 2-16. In a particular aspect, the oritavancin drug substance preparation has about 90% purity or greater by peak area relative to impurities 2-16. In a further particular aspect, the oritavancin drug substance preparation has about 96% purity or greater by peak area relative to impurities 2-16. In another particular aspect, the oritavancin drug substance preparation has a purity of between about 85 and 90%, between about 86 and 91%, between about 87 and 92%, between about 88 and 93%, between about 89 and 94%, between about 90 and 95%, between about 90 and 96%, between about 91 and 96%, or between about 92 and 97%, by peak area relative to impurities 2-16.

Suitable pharmaceutically acceptable excipients include, but are not limited to mannitol, sorbitol, sucrose and trehalose. In a particular aspect, the pharmaceutically acceptable excipient is mannitol. The ratio of the drug substance preparation to the one or more excipients may vary and includes 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, and 1:10 wt/wt. Stated in another fashion, the pharmaceutical compositions of the invention comprise oritavancin drug substance preparation in a range of about 50-75% and one or more pharmaceutically acceptable excipients in a range of about 50-25% by weight of the pharmaceutical composition. In one aspect, the pharmaceutical compositions of the invention comprise oritavancin drug substance preparation in a range of about 55-70% and one or more pharmaceutically acceptable excipients in a range of about 45-30%, by weight. In another aspect, the pharmaceutical compositions of the invention comprise oritavancin drug substance preparation in a range of about 56-68% and one or more pharmaceutically acceptable excipients in a range of about 44-32%, by weight. In a further aspect, the pharmaceutical compositions of the invention comprise oritavancin drug substance preparation in a range of about 16-21% and one or more pharmaceutically acceptable excipients in a range of about 84-79%, by weight. In certain aspects, the amount of oritavancin drug substance preparation in a pharmaceutical composition is not more than about 70%, 69%, 68%, 67%, 66%, 65%, 64%, 63%, 62%, 61%, 60%, 59%, 58%, 57%, 56%, 55%, 54%, 53%, 52%, 51% or 50%, by weight of the composition, with the remainder of the weight comprising the one or more pharmaceutically acceptable excipients, moisture and counterions.

The pharmaceutical composition comprising an oritavancin drug substance preparation of the present invention may be further characterized by its stability over time. In one aspect, the pharmaceutical compositions of the present invention exhibit less than a 1.0% increase by peak area in the level of impurities 2 and 10 within 36 months when stored at about room temperature. In other aspects, the increase is less than a 0.1%, 0.2%, 0.3%, 0.4%, 0.6%, 0.7%, 0.8%, 0.9%, or 1.0% increase over 2, 4, 6, 8, 10, 12, 14, 16, 18, 20, 22, 24, 26, 28, 30, 32, 34, 36, 38, 40, 42, 44, 46, 48, 50, 52, 54, 56, 58, 60 or more months. In another aspect, the pharmaceutical compositions of the present invention exhibit less than a 2.0% increase by peak area in the level of impurities 2-16 within 36 months. In other aspects, the increase is less than a 0.1%, 0.2%, 0.3%, 0.4%, 0.6%, 0.7%, 0.8%, 0.9%, or 1.0% increase over 2, 4, 6, 8, 10, 12, 14, 16, 18, 20, 22, 24, 26, 28, 30, 32, 34, 36, 38, 40, 42, 44, 46, 48, 50, 52, 54, 56, 58, 60.

The pharmaceutical composition comprising an oritavancin drug substance preparation of the present invention may also be characterized by its pH. The pharmaceutical composition comprising an oritavancin drug substance preparation may have a pH of between 2.0 and 5.0, between 2.5 and 4.5, between 3.0 and 4.5, between 3.0 and 4.0, between 3.5 and 4.5, or be a pH of about 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 or 5.0.

Methods for Preparing Pharmaceutical Compositions Comprising Oritavancin Drug Substance Preparations The present invention also includes methods of preparing the pharmaceutical compositions comprising an oritavancin drug substance preparation of the present invention (i.e., a drug substance preparation of oritavancin, or a salt thereof, wherein a minimum level of purity (or a maximum level of impurity) has been achieved) and one or more pharmaceutically acceptable excipients.

In a particular embodiment, the method of preparing a pharmaceutical composition comprising the steps of:
a) dissolving one or more pharmaceutically acceptable excipients in water having a pH of 2.5 to 3.5 to form a solution,
b) dissolving oritavancin drug substance preparation in the solution of a) and adjusting the pH of the solution to 3.0 to 4.5,
c) filtering the solution of b), and
d) lyophilizing the filtered solution of c), thereby preparing pharmaceutical compositions comprising drug substance preparations of the present invention. Such pharmaceutical compositions include (i) a pharmaceutical composition comprising an oritavancin drug substance preparation of the present invention and one or more pharmaceutically acceptable excipients, wherein the oritavancin drug substance preparation has a maximum impurity level of not more than 5.5% by peak area of impurity 2 and impurity 10, defined by peaks B and J of FIG. 2, respectively; and (ii) a pharmaceutical composition comprising an oritavancin drug substance preparation of the present invention and one or more pharmaceutically acceptable excipients, wherein the oritavancin drug substance preparation has about 85% purity or greater by peak area relative to impurities 2-16, defined by peaks B-P of FIG. 2, respectively.

In certain aspects of the method, the filtered solution of c) is added to a sterilized vial prior to the lyophilizing of d).

In certain aspects of the method, the pH is adjusted in b) to between 3.1 and 4.4, between 3.2 and 4.3, between 3.3 and 4.3, between 3.4 and 4.2, between 3.5 and 4.1, between 3.5 and 4.0, between 3.6 and 3.9, between 3.6 and 3.8, or between 3.7 and 4.2.

In certain aspects of the method, the lyophilizing achieves a level of moisture of less than about 7.0%, 6.5%, 6.0%, 5.5%, 5.0%, 4.5%, 4.0%, 3.5%, 3.0%, 2.5%, 2.0%, 1.5%, 1% or 0.5% by weight.

Suitable means for adjusting the pH of the solution include, but are not limited to, adding phosphoric acid to the solution until the desired pH is achieved.

Suitable means for filtering the solution of b) include, but are not limited to, the use of 0.45 and 0.22 μm filters in sequence.

The present invention also encompasses pharmaceutical compositions prepared by the methods provided herein.

Drug Product Comprising Pharmaceutical Compositions

The present invention includes drug products or dosage forms comprising a pharmaceutical composition of the present invention (i.e., a pharmaceutical composition comprising an oritavancin drug substance preparation of the present invention (i.e., a drug substance preparation of oritavancin, or a salt thereof, wherein a minimum level of purity (or a maximum level of impurity) has been achieved)) and one or more additional pharmaceutically acceptable excipients.

In one aspect of the invention, the level of purity/impurity of the oritavancin drug substance preparation is defined by the peak area of one or more selected impurities on an HPLC chromatogram. In a particular embodiment, the drug product or dosage form comprises a pharmaceutical composition of the present invention and one or more additional pharmaceutically acceptable excipients, wherein the oritavancin drug substance preparation has about 85% purity or greater by peak area relative to impurities 2-16, defined by peaks B-P of FIG. 2, respectively. In alternative aspects, the oritavancin drug substance preparation has a purity of about 86%, 87%, 88%, 89%, 90%, 91%, 92%, 93%, 94%, 95%, 96%, 97%, 98% or 99% or greater by peak area relative to impurities 2-16. In a particular aspect, the oritavancin drug substance preparation has about 90% purity or greater by peak area relative to impurities 2-16. In a further particular aspect, the oritavancin drug substance preparation has about 96% purity or greater by peak area relative to impurities 2-16. In another particular aspect, the oritavancin drug substance preparation has a purity of between about 85 and 90%, between about 86 and 91%, between about 87 and 92%, between about 88 and 93%, between about 89 and 94%, between about 90 and 95%, between about 90 and 96%, between about 91 and 96%, or between about 92 and 97%, by peak area relative to impurities 2-16.

Suitable pharmaceutically acceptable excipients include, but are not limited to mannitol, sorbitol, sucrose and trehalose. In a particular aspect, the pharmaceutically acceptable excipient is mannitol. The ratio of the drug substance preparation to the one or more excipients may vary and includes 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, and 1:10 wt/wt.

The drug product or dosage form comprising a pharmaceutical composition of the present invention may be further characterized by its stability over time. In one aspect, the drug products or dosage forms of the present invention exhibit less than a 0.5% increase by peak area in the level of impurities 2-16 within 3 months. In other aspects, the increase is less than a 0.1%, 0.2%, 0.3%, 0.4%, 0.6%, 0.7%, 0.8%, 0.9%, or 1.0% increase over 1, 2, 3, 4, 5, 6, 7, 8, 9, 10, 11, 12 or more hours, 1, 2, 3, 4, 5, 6, 7, 8, 9, 10, 11, 12 or more days, 1, 2, 3, 4, 5, 6, 7, 8 or more weeks, or 1, 2, 3, 4, 5, 6 or more months.

The drug product or dosage form comprising a pharmaceutical composition of the present invention may also be characterized by its pH. The drug product or dosage form may have a pH of between 2.0 and 5.0, between 2.5 and 4.5, between 3.0 and 4.5, between 3.0 and 4.0, between 3.5 and 4.5, or be a pH of about 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 or 5.0.

Methods for Preparing Drug Products Comprising Pharmaceutical Compositions

The present invention also includes methods of preparing drug products or dosage forms comprising a pharmaceutical composition of the present invention (i.e., a pharmaceutical composition comprising an oritavancin drug substance preparation of the present invention (i.e., a drug substance preparation of oritavancin, or a salt thereof, wherein a minimum level of purity (or a maximum level of impurity) has been achieved)) and one or more additional pharmaceutically acceptable excipients.

In a particular embodiment, the method for preparing a drug product or dosage form comprising a pharmaceutical composition of the present invention and one or more additional pharmaceutically acceptable excipients comprises dissolving a pharmaceutical composition of the present invention in Water for Injection or 5% dextrose in water to form a solution, thereby preparing a drug product or dosage form comprising a pharmaceutical composition of the present invention. Such drug products or dosage forms include a drug product or dosage form comprising a pharmaceutical composition of the present invention and one or more additional pharmaceutically acceptable excipients, wherein the oritavancin drug substance preparation has about 85% purity or greater by peak area relative to impurities 2-16, defined by peaks B-P of FIG. 2, respectively.

In certain aspects, the concentration of oritavancin in the solution is from about 0.5-100, 1-50, 2.5-40, 5-30, 7.5-25, 0.5-50, 0.5-40, 0.5-30, 5-100, 5-50 or 5-50 mg/mL.

The present invention also encompasses drug products prepared by the methods provided herein.

High Purity Chloroeremomycin

Figure 3:
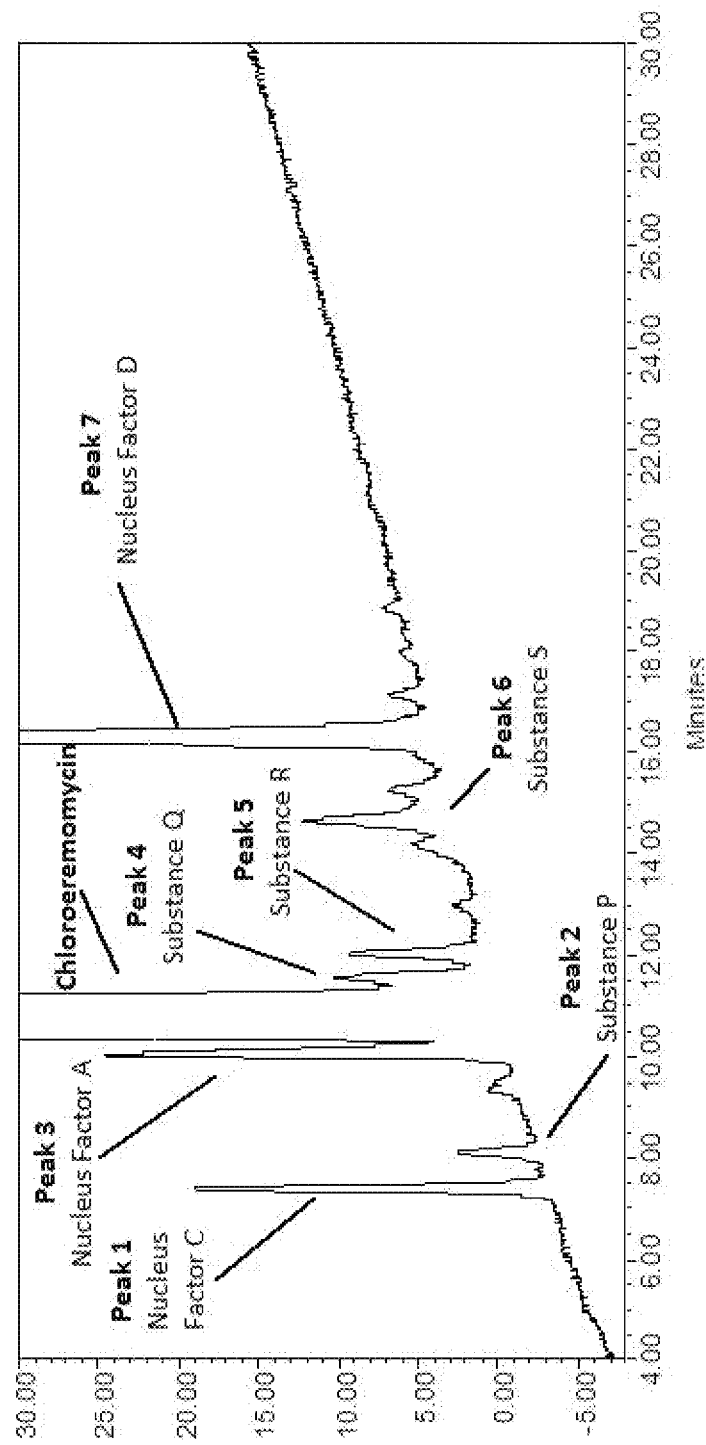
FIG. 3 is an HPLC chromatogram of a chloroeremomycin preparation.

The present invention includes high purity chloroeremomycin, or a salt thereof. In one aspect of the invention, the level of purity/impurity of the chloroeremomycin is defined by the peak area of one or more selected impurities on an HPLC chromatogram. In a particular embodiment the invention is directed to high purity chloroeremomycin, or a salt thereof, having a maximum impurity level of not more than 25.0% by peak area of impurities nucleus factors A, C and D, and substances P, Q, R, and S, defined by peaks 3, 1, 7, 2, 4, 5 and 6 of FIG. 3, respectively. In alternative aspects, the chloroeremomycin, or a salt thereof, has a maximum impurity level of not more than 24.5%, 24%, 23.5%, 23%, 22.5%, 22%, 21.5%, 21%, 20.5%, 20%, 19.5%, 19%, 18.5%, 18%, 17.5%, 17%, 16.5%, 16%, 15.5%, 15%, 14.5%, 14%, 13.5%, 13%, 12.5%, 12%, 11.5%, 11%, 10.5%, 10% or less by peak area of impurities nucleus factors A, C and D, and substances P, Q, R, and S, defined by peaks 3, 1, 7, 2, 4, 5 and 6 of FIG. 3. In a particular aspect, the chloroeremomycin, or a salt thereof, has a maximum impurity level of not more than 18% by peak area of impurities nucleus factors A, C and D, and substances P, Q, R, and S, defined by peaks 3, 1, 7, 2, 4, 5 and 6 of FIG. 3.

In another particular embodiment, the high purity chloroeremomycin, or a salt thereof, has a purity of 80% purity or greater. In alternative aspects, the high purity chloroeremomycin, or a salt thereof, has a purity of about 81%, 82%, 83%, 84%, 85%, 86%, 87%, 88%, 89%, 90%, 91%, 92%, 93%, 94%, 95%, 96%, 97%, 98% or 99% or greater. In a particular aspect, the high purity chloroeremomycin, or a salt thereof, has a purity of about 82% or greater. In a further particular aspect, the high purity chloroeremomycin, or a salt thereof, has a purity of about 90% or greater. In another particular aspect, the high purity chloroeremomycin, or a salt thereof, has a purity of between about 80 and 95%, between about 81 and 95%, between about 82 and 95%, between about 83 and 95%, between about 85 and 95%, between about 86 and 95%, between about 87 and 95%, between about 88 and 95%, or between about 89 and 95%.

The high purity chloroeremomycin of the present invention may be further characterized by its stability over time. In one aspect, the high purity chloroeremomycin of the present invention exhibit less than a 1.0% increase by peak area in the level of impurities 3, 1, 7, 2, 4, 5 and 6 within 12 months under refrigerated conditions. In other aspects, the increase is less than a 0.1%, 0.2%, 0.3%, 0.4%, 0.6%, 0.7%, 0.8%, 0.9%, or 1.0% increase over 1, 2, 3, 4, 5, 6, 7, 8, 9, 10, 11, 12, 13, 14, 15, 16, 17, 18, 19, 20, 21, 22 or more months. In another aspect, the high purity chloroeremomycin of the present invention exhibit less than a 2.0% increase in the level of impurities within 12 months under refrigerated conditions. In other aspects, the increase is less than a 0.1%, 0.2%, 0.3%, 0.4%, 0.6%, 0.7%, 0.8%, 0.9%, or 1.0% increase over 1, 2, 3, 4, 5, 6, 7, 8, 9, 10, 11, 12, 13, 14, 15, 16, 17, 18, 19, 20, 21, 22 or more months.

Methods for Preparing High Purity Chloroeremomycin

The present invention also includes methods of preparing high purity chloroeremomycin, or a salt thereof.

In a particular embodiment, the method for preparing high purity chloroeremomycin, or a salt thereof, comprising the steps of:

a) growing a culture of a chloroeremomycin-producing microorganism under fermentative conditions in a medium free of animal-sourced material (ASM) and under conditions promoting biosynthesis of chloroeremomycin by the culture,
b) recovering chloroeremomycin from fermentation broth of a) using a polymeric exchange resin,
c) decolorizing the chloroeremomycin recovered in b) using a polymeric adsorbent resin, chromatographically separating the decolorized chloroeremomycin using a hydrophobic polymeric resin column, and precipitating the separated chloroeremomycin using an organic solvent, and
d) drying the chloroeremomycin crystals, thereby preparing high purity chloroeremomycin or a salt thereof. Such high purity chloroeremomycin, or a salt thereof, includes chloroeremomycin having a maximum impurity level of not more than 18.0% by peak area of impurities nucleus factors A, C and D, and substances P, Q, R, and S, defined by peaks 3, 1, 7, 2, 4, 5 and 6 of FIG. 3, respectively.

In the method for preparing high purity chloroeremomycin described above, the chloroeremomycin-producing microorganism may be any microorganism that innately produces chloroeremomycin or that is engineered to produce chloroeremomycin. Suitable microorganisms include, but are not limited to, one or more microorganisms of the following genera: *Nocardia, Amycolatopsis* and *Kibdelosporangium*. In a particular aspect, the chloroeremomycin-producing microorganism is *Kibdelosporangium aridum*.

The fermentative conditions of step (a) generally involve the use of sources of carbohydrates, nitrogen, oligoelements, cations and phosphate at 30-35° C.

The medium free of animal-sourced material (ASM) is media that is supplemented with a nitrogen source that is not derived from animal. Suitable sources of nitrogen that may be used in the media include, but are not limited to, enzymatic digests of soybean meal/flour. The critical factor is that it serves as a source of organic nitrogen. Suitable media includes, but is not limited to, aqueous solutions of magnesium, calcium, potassium, phosphate and primary grown yeast.

Conditions promoting biosynthesis of chloroeremomycin by the culture include, but are not limited to, a temperature range of 20-40° C. and aeration and agitation rates that are sufficient to maintain growth of the microorganism.

Suitable polymeric exchange resins for use in recovering chloroeremomycin from the fermentation broth include, but are not limited to, sulfonated macroporous copolymers of styrene and divinylbenzene.

Suitable polymeric adsorbent resins for use in decolorizing the chloroeremomycin recovered include, but are not limited to, non-functionalized macroporous copolymers of styrene and divinylbenzene.

Suitable hydrophobic polymeric resin columns for use in chromatographically separating the decolorized chloroeremomycin include, but are not limited to, non-functionalized macroporous copolymers of styrene and divinylbenzene.

Suitable organic solvents for use in precipitating the separated chloroeremomycin include, but are not limited to, methanol.

Suitable means for drying the chloroeremomycin crystals include, but are not limited to, drying on a tray or in a Nutsche filter at elevated temperature and reduced pressure.

The method for preparing high purity chloroeremomycin, or a salt thereof, may include some additional optional steps. For example, a concentrating step and a precipitating step may be performed after the decolorization and prior to the chromatography. The concentrating step may be performed by distillation of the volatile solvents under reduced pressure. The precipitating step may be performed by adjustment of the solution to an alkaline pH. In addition, a concentrating step may be performed after chromatography and prior to precipitation. This concentrating step may be performed by distillation of the volatile solvents under reduced pressure. Further, the decolorized chloroeremomycin may be chromatographically separated on reverse phase silica gel rather than using a hydrophobic polymeric resin column.

The present invention also encompasses high purity chloroeremomycin prepared by the methods provided herein.

Means for Measuring Purity

The level of purity of oritavancin or an oritavancin drug substance preparation, or of an oritavancin drug substance preparation in a pharmaceutical composition, a drug product, or a dosage form, can be determined by HPLC. In particular aspects, the purity level is measured by HPLC, wherein the HPLC method includes a C18 reverse-phase stationary phase and a gradient of mobile phase B, which is phosphoric acid/water/acetonitrile/tetrahydrofuran at a ratio of about 1/1000/1500/25 (v/v/v/v), in mobile phase A, which is phosphoric acid/water/tetrahydrofuran at a ratio of about 1/1000/10 (v/v/v).

The level of purity of chloroeremomycin, or chloroeremomycin in a drug substance preparation, pharmaceutical composition, drug product, and dosage form comprising chloroeremomycin can also be determined by HPLC. In particular aspects, the purity level of the chloroeremomycin is measured by HPLC, wherein the HPLC method includes a phenyl derivatized reverse-phase stationary phase and a gradient of mobile phase B, which is acetonitrile/water/formic acid/triethylamine at a ratio of about 40/60/0.2/0.03 (v/v/v/v) in mobile phase A, which is water/formic acid/triethylamine at a ratio of about 100/0.2/0.03 (v/v/v).

Means for Determining Peak Area from HPLC Chromatograms

The area of impurity peaks on HPLC chromatograms can be determined by standard chromatogram integration software such as, but not restricted to ChemStation from Agilent, Empower from Waters, LabSolutions from Shimadzu.

Vials Comprising Pharmaceutical Composition

The present invention is also directed to a vial containing a lyophilized powder comprising a pharmaceutical composition of the present invention. In certain aspects, the vial is a glass vial that was stoppered under a chemically inert dry gas. Suitable chemically inert dry gases include, but are not limited to, nitrogen and argon.

III. Examples

1) Manufacturing Process and Process Controls Overview

Oritavancin drug substance (DS) is a semi-synthetic glycopeptide manufactured in two stages. The first stage involves classical fermentation using a strain of the bacterium *Kibdelosporangium aridum* derived by strain improvement techniques from strain NRRL 18098 to produce the intermediate nucleus factor B (chloroeremomycin). The second stage is a synthetic step involving reductive alkylation of nucleus factor B to produce oritavancin drug substance. The manufacturing process of nucleus factor B and oritavancin diphosphate is depicted in the flow charts provided in FIG. 4 and FIG. 5, respectively.

2) Manufacture of Nucleus Factor B

The manufacture of nucleus factor B involves fermentation, recovery, purification and precipitation, provided as follows.

A. Fermentation

Fermentation used to produce nucleus factor B (from the working stock vial to the production fermentor) is a classical fermentation process used to produce cell mass. Nucleus factor B is the product of the cellular metabolism of the cells and is dictated by the native genetic make-up of the culture. The producing culture is *Kibdelosporangium aridum*.

Inoculum Flask/Shake Flask

The purpose of this step in the nucleus factor B fermentation process was to provide sufficient biomass to achieve adequate growth of the culture in the subsequent seed fermentor step.

An inoculum flask (shake flask) was inoculated with the whole or part of a frozen working stock vial of *Kibdelosporangium aridum*. Shake flask medium was autoclaved at 120-127° C. for not less than 20 minutes prior to inoculation. The inoculum flask was incubated on a rotary shaker to support the growth of the culture leading to an increase in cell mass. The actively growing cells of the inoculum flask were used to inoculate the seed fermentor.

The typical composition of the inoculum flask medium is listed in Table 1. The medium contains water, and carbon and nitrogen sources that support the growth of the culture. Previously, some of the raw materials used for the growth medium in the fermentation stage contained digests of animal tissue. The methodology provided herein is limited to the use of animal-sourced material (ASM)-free reagents, and oritavancin produced without these materials is termed ASM-free oritavancin drug substance preparation. The carbon and nitrogen sources are interchangeable with other like ingredients listed in Table 2, and the concentrations may be varied to provide consistent growth. For control experiments in which ASM-containing reagents were used, digests of animal tissues (such as pig skin digests) were used in place of digests of plant based materials (such as phytone, a digest of soybean meal/flour, Table 1). For all experiments, the nominal operating temperature for the inoculum flask was 33±2° C. with an agitation rate of 240±10 RPM. Operation outside of the temperature and agitation range was acceptable provided good growth was apparent. Suitable growth was determined by measuring cell density (optical density measurement of the media at 600 nm) and obtaining a minimum optical density of 7 and typically 10-15. The typical cycle time for the shake flask was 40 hours. The growing culture was also checked for purity or absence of other microorganisms.

TABLE 1

Materials used in Inoculum Flask Media

| Component | Typical Medium Composition (g/L) |
| --- | --- |
| Dextrose monohydrate | 15.0 |
| Yeast extract | 9.0 |
| Phytone (papaic digest of soybean meal) | 10.0 |
| Soluble starch | 10.0 |
| Mops buffer (3-(N-morpholino propanesulfonic acid) | 2.1 |
| Defoamer | 1-2 drops |
| Tap water | To volume |

TABLE 2

Carbon and Nitrogen Sources

Water, Tap
Ammonia water, 18%
Ammonia water, 28%
Ammonium sulfate, FCC
Calcium carbonate, ACS grade
Calcium carbonate, precipitated
Calcium carbonate, Technical, powder
Cobaltous chloride hexahydrate (ACS)
Corn Starch
Corn syrup, D.E.95
Corn syrup, D.E.95, Aqueous Dilution
Cupric sulfate
Dextrose monohydrate (Not USP), Powder
Glycerol
Starch, soluble, not NF
Magnesium sulfate crystals, Epsom Salts, Technical
Magnesium sulfate, technical, anhydrous
Magnesium sulfate, USP (heptahydrate)
Soybean Protein, Hydrolyzed, Technical
Glycerol, USP/EP
Potassium chloride, USP
Potassium phosphate, monobasic, not NF
Potato Dextrin (Perfectamyl B1102)
Sodium Chloride
Sodium hydroxide, NF, pellets
Sodium hydroxide solution, 50% caustic soda
Soybean flour, Special grade
Soybean meal, Papaic digest (Phytone)
Buffer, 3-(N-Morpholino) Propanesulfonic Acid
Acid, Sulfuric, 66, Food Chemicals Codex
Acid, Sulfuric, reagent grade
Acid, Sulfuric, Technical
Potassium Chloride, USP
Yeast extract
Yeast extract (Tastone 154)
Yeast extract, autolyzed
Yeast, brewers, dried
Yeast, Dried Seed Fermentor The purpose of this step in the nucleus factor B fermentation process was to provide sufficient biomass to achieve adequate growth of the culture in the subsequent production fermentor step.

The seed fermentor cycle time (age), as well as the environmental control process variables (temperature, aeration, agitation and back pressure), were controlled to ensure growth consistency and productivity (yield). The size of the seed fermentor batch was a function of the inoculum volume desired for transfer into the production fermentor. Typically, a seed inoculum volume of 3% to 10% of the production fermentor volume provided a sufficient number of cells for optimum growth and productivity (yield) in the production fermentor. A typical volume of the seed batch was 3000 L for a production fermentor of 42000 L.

The seed fermentor medium was steam heat treated at 121° C. to 125° C. for 45±5 minutes, cooled to the inoculation temperature, and then aseptically inoculated from the contents of the inoculum flask. The seed fermentor medium was prepared using ingredients selected from the raw materials listed in Table 2. Animal-sourced materials were only used in experimental controls. The seed fermentor was agitated, aerated and maintained at constant temperature. Positive backpressure was maintained on the seed fermentor after heat treatment to prevent the entry of adventitious organisms. The actively growing cells of the seed fermentor were used to aseptically inoculate the production fermentor.

The typical composition of seed fermentor medium is listed in Table 3. The medium contains water, minerals, vitamins, organic and inorganic salts, defoamers, and carbon, nitrogen and phosphate sources that support the growth of the culture. The ingredients are interchangeable with other like ingredients (i.e. dextrose could be substituted with glucose) listed in Table 2 and the concentrations may be varied to provide consistent growth. For control experiments in which ASM-containing reagents were used, trypticase Soy Broth (containing a digest of bovine milk casein) and soytone (porcine pancreatic digest of soybean meal) was used in place of Hy-Soy (Table 3).

TABLE 3

Materials Used in Seed Fermentation Media

| Component | Typical Medium Concentration (g/L) |
|---|---|
| Hy-Soy (hydrolyzed soybean protein) | 5.0 |
| Yeast, primary grown | 5.0 |
| Corn starch | 5.0 |
| Calcium carbonate | 1.0 |
| Dextrose monohydrate | 10.0 |
| Defoamer | 0.3 |
| Tap water | To Volume |

The temperature of the seed fermentor was maintained at a controlled temperature target between 20° C. and 40° C., until a suitable amount of cell mass was achieved in all experiments. The agitation and aeration rates were dependent on the size of the seed fermentor and were varied to effect adequate oxygen transfer. Brief excursions outside of these ranges were acceptable, provided good growth was apparent. Growth and viability were monitored through indirect measurements of metabolic process variables including pH and oxygen consumption, and directly through microscopic examination. The seed fermentor was checked for presence of foreign growth by performing purity testing. These tests included standard Gram staining of the growing culture and Gram stain of the culture grown in a general purpose medium, Casein Soybean Digest Broth. The presence of the organism of choice and the absence of adventitious microorganisms was confirmed. The pure culture from the seed fermentor was then released to be used in the production fermentor. The typical cycle time required to achieve growth at this stage was about 42 to 60 hours. The typical operating conditions of the seed fermentor are provided in Table 4.

TABLE 4

Seed Fermentor Operation Conditions

| Operational Condition | Typical Target Set point |
|---|---|
| Temperature | 32 ± 0.5° C. |
| Sparge Airflow | 100 cfm |

TABLE 4-continued

Seed Fermentor Operation Conditions

| Operational Condition | Typical Target Set point |
|---|---|
| Agitation | 100 rpm |
| Back-Pressure | 10 psig |

CFM = cubic feet per minute;
PSI = pound per square inch;
RPM = rotations per minute.

Production Fermentor

The purpose of the production fermentor was to propagate the culture to a high cell density and to maintain the viability of this cell mass for a sufficient period of time for the biosynthesis of nucleus factor B by the culture.

The production fermentor cycle time (age), as well as the environmental control process variables (temperature, agitation, aeration, pH and back-pressure), were controlled within an operating range to ensure growth consistency and productivity (yield). The size of the production fermentor was a function of the volume of cell mass desired for transfer to the recovery process. The production fermentor volume ranged between 18,000 L and 60,000 L with a typical fermentor volume of 42,000 L.

The production fermentation medium was steam heat treated at 121 to 125° C. for 40±5 minutes. The production fermentor was inoculated aseptically with the culture produced in the seed fermentation step. The production fermentor medium was prepared using ingredients selected from the raw materials listed in Table 2. Animal-sourced materials were only used in experimental controls. Positive backpressure was maintained on the production fermentor after heat treatment to prevent the entry of adventitious organisms.

The typical composition of production fermentor medium is listed in Table 5. The medium contains chemically defined ingredients and complex agricultural products. Additionally, the nutrients required for growth of the organism are provided through multiple ingredients to compensate for potential variability associated with the complex raw materials used in the process. The raw materials include water, minerals, vitamins, organic and inorganic salts, defoamers, and carbon, nitrogen and phosphate sources that support the growth of the culture. The ingredients are interchangeable with other like ingredients (i.e. Soy flour can be substituted with soy grits) listed in Table 2 and the concentrations may be varied to provide consistent growth. Additionally, carbon and/or nitrogen sources can also be fed into the fermentation to sustain viability of the culture and to provide consistency and productivity (yield). For control experiments in which ASM-containing reagents were used, peptone PSR #5 (pig skin enzymatic digest) was used in place of soybean flour (Table 5).

TABLE 5

Materials for Production Fermentation

| Component | Typical Medium Concentration (g/L) |
|---|---|
| ASM Free Medium | |
| Soybean flour | 6.0 |
| Primary grown yeast | 6.5 |
| Corn syrup (DE95) | 80.4 |
| Potassium chloride (USP) | 5.4 |
| Magnesium sulfate crystals | 1.2 |
| Potassium phosphate, monobasic | 0.17 |

TABLE 5-continued

Materials for Production Fermentation

| Component | Typical Medium Concentration (g/L) |
|---|---|
| Ammonium sulfate, FCC | 4.4 |
| Calcium carbonate | 4.9 |
| Defoamer | 1.0 |
| Ammonia water | 17 |
| Tap water | To Volume |

FCC = Food Chemicals Codex;
USP = United States Pharmacopeia

The temperature of the production fermentor was maintained at a controlled temperature target between 20° C. and 40° C. to promote cell growth and to maintain viability of the cell mass in all experiments. The agitation and aeration rates were dependent on the size of the production fermentor and were varied to effect adequate oxygen transfer. The pH of the production fermentor was controlled to 6.6 to 6.8 in order to maintain viability of the culture. Brief excursions outside of these ranges were acceptable, provided good growth was apparent. Sugar and ammonia water was fed throughout fermentation cycle for sustained growth and biosynthesis of nucleus factor B. Growth and viability were monitored through indirect measurements of metabolic process variables including pH, oxygen, glucose, and ammonium consumption. Microscopic examination of the media was also performed. The broth was sampled daily throughout the fermentation cycle and tested for foreign growth. These tests included standard Gram staining of the growing culture and Gram stain of the culture grown in a general purpose medium, Casein Soybean Digest Broth. The presence of the organism of choice and the absence of adventitious microorganisms was confirmed. The total length of fermentation cycle was typically between 284±8 hours. The harvest age of the fermentation was a function of the desired batch yield and cell viability and was not a critical process decision. Harvesting the fermentation with shorter cycle resulted in lower fermentation batch titer whereas extending the fermentation cycle time did not improve batch titer due to unsustainable viability. The culture was harvested at the end of the cycle and transferred for recovery of nucleus factor B. The production fermentor stage of the process served to promote cell growth and synthesis of nucleus factors. The typical operating conditions of the production fermentor are provided in Table 6 for all experiments.

The titer yield of nucleus factor B in the fermentation was a function of cell growth, media concentration, and fermentation cycle and was typically within a range of 2 to 4 g/L. The titer yield of nucleus factor B was determined after completion of fermentation.

TABLE 6

Typical Production Fermentor Operation Conditions

| Operational Condition | Typical Target Set point |
|---|---|
| Temperature | 34.5 ± 0.5° C. |
| Sparge Air | 1000 CFM |
| Agitation | 125 RPM |
| Back-Pressure | 10 psig |
| pH | 6.7 ± 0.2 |

CFM = cubic feet per minute;
PSI = pound per square inch;
RPM = rotations per minute.

B. Recovery

Factor Capture

The purpose of these steps was to separate nucleus factor B and glycopeptide related substances from the fermentation broth. The fermentation broth was mixed for about 6 hours with a polymeric cation exchange resin, and warmed to approximately 50° C. to adsorb the nucleus factors onto the resin. The resin was separated from the spent broth by filtration and washed with water.

Nucleus factor B and related structures were desorbed from the resin by mixing with alkaline water. The resin was subsequently washed with water and separated. The eluates and washes containing the desorbed nucleus factors were collected and combined. The pH of the combined eluate and washes was adjusted to pH 6.5 to 9.6. The factor capture eluate was filtered and tested for nucleus factor B concentration.

C. Purification

Decolorization

The purpose of these steps was to remove colored components from the factor capture eluate. The nucleus factors in the pooled factor capture eluate and washes were adsorbed onto a polymeric adsorbent resin and the resin was washed with water. The nucleus factors were eluted using an aqueous isopropyl alcohol and acetic acid solution.

In some instances, the factor capture eluate was processed as multiple decolorization batches. The decolorization batches were then pooled to form the decolorization pool. The decolorization pool was tested for the concentration of the four nucleus factors [A+B+C+D].

Chromatographic Separation

The purpose of these steps was to purify the nucleus factor B in the decolorization pool. The decolorization pool pH was adjusted to 6.5 to 8.9 using ammonium hydroxide. The pool was diluted with purified water to control the IPA content according to the following specification:

If the solution pH≥7.5, then the IPA content was adjusted to NMT 3.0% v/v;

If the solution pH≤7.5, then the IPA content was adjusted to NMT 1.5% v/v.

The solution was loaded onto a polystyrene divinylbenzene resin column (loading NMT 50 g total combined Factors [A+B+C+D] per L of resin).

The column was successively eluted with NLT 1.8 BV (bed volumes) of 1% v/v isopropanol in aqueous ammonium phosphate buffer, NLT 1.8 BV of 3% v/v isopropanol in aqueous monobasic ammonium phosphate buffer, and finally 5% v/v isopropanol in aqueous monobasic ammonium phosphate buffer. One bed volume was defined as the volume of resin in the column. Select early and late fractions were analyzed by HPLC against the minimum fraction quality criteria of NLT 70 PA % Factor B; NMT 8 PA % Factor A; and NMT 6 PA % Factor C.

Early and late fractions passing the minimum fraction quality criteria were pooled with the fractions bracketed in between them. In some instances, the fraction pool pH was adjusted using phosphoric acid and/or ammonium hydroxide. The fraction pool quality was verified by HPLC against the Fraction Pool Specifications listed in Table 7.

TABLE 7

Fraction Pool Specifications

| Compound | Acceptance Criteria (Peak Area %) |
|---|---|
| Nucleus Factor B | NLT 80.0% |
| Nucleus Factor A | NMT 5.0% |

TABLE 7-continued

Fraction Pool Specifications

| Compound | Acceptance Criteria (Peak Area %) |
| --- | --- |
| Nucleus Factor C | NMT 1.9% |
| Nucleus Factor D | NMT 10.0% |
| Sum of Nucleus Factors A + C | NMT 5.0% |
| RS-Q (RRT 1.08) | NMT 5.0% |
| Single Largest Unspecified Substance (SLUS) | NMT 2.0% |

Abbreviations:
NLT = not less than;
NMT = not more than.

Concentration (Ultrafiltration/Diafiltration)

The pooled fractions were partially concentrated by ultrafiltration and the concentrate (referred to as the retentate) was diafiltered with purified water. The diafiltered retentate pH was adjusted to 9.6 to 10.5 using aqueous sodium hydroxide and/or acetic acid and diafiltered again using NLT 2.8 diafiltration volumes (DV) of purified water. One DV was defined as the volume of the retentate.

The retentate was assayed by ion chromatography for phosphate and diafiltration was terminated when the phosphate concentration was NMT 0.40 mg/mL. The retentate was acidified with acetic acid to form the acetate salt and in some instances was further concentrated and/or diafiltered. The retentate was diluted as needed with purified water. The nucleus factor B concentration in the retentate was determined by HPLC.

D. Precipitation

Salt Precipitation

The aqueous solution was heated and mixed with methanolic sodium acetate. Precipitation was assisted by seeding with isolated nucleus factor B as needed. The slurry was cooled, additional methanolic sodium acetate was added and the slurry was further cooled. The precipitated nucleus factor B diacetate salt was collected by centrifugation and washed with NLT 3 L of methanol per kg of nucleus factor B.

Drying and Milling

The wet cake was dried under reduced pressure at NMT 45° C. for NMT 48 hours, or alternatively, at NMT 35° C. for NMT 96 hours. Drying was monitored by gas chromatography with an in-process limit of NMT 7% w/w residual solvents. In some instances, the dried material was mechanically delumped and blended. The dried material was stored at NMT 8° C.

Figure 7A:
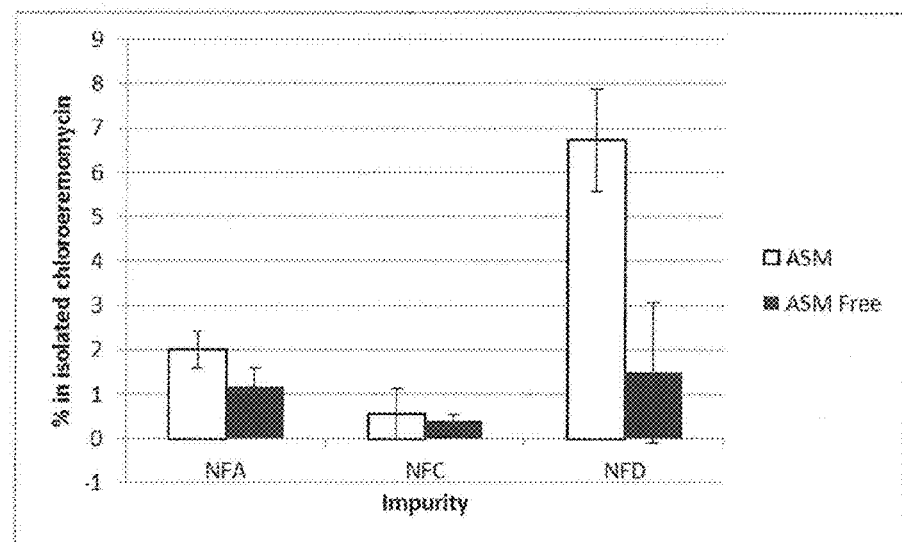
FIGS. 7A-7B provide the results from HPLC testing of the levels of certain impurities in nucleus factor B (FIG. 7A) and oritavancin (FIG. 7B) preparations.

The levels of certain impurities in the dried material were determined via HPLC. As can be seen in FIG. 7A, the levels of certain impurities were reduced when ASM-free media was used.

The Factor Capture, Decolorization, Chromatographic Separation, Concentration (Ultrafiltration/Diafiltration), Precipitation and Drying steps may be performed as multiple batches. A typical overall recovery of nucleus factor B is 20-50% of the estimated nucleus factor B Kg in the fermentation broth.

3) Manufacture of Oritavancin Diphosphate (Reductive Alkylation)

The steps involved in the synthetic conversion of nucleus factor B to oritavancin drug substance include reductive alkylation, chromatographic separation, concentration by ultrafiltration and diafiltration, salt crystallization, and drying. The reaction stoichiometry is provided in Table 8.

TABLE 8

Reaction Stoichiometry

| Material[a] | Factor (Kg/Kg) | Molar Equivalents |
| --- | --- | --- |
| Nucleus Factors Charge Factor[b] | 1.0 | 1.0 |
| Copper (II) acetate monohydrate | 0.099-0.166 | 0.9-1.3 |
| Methanol[c] | 55.9-83.8 | N/A |
| 4-Chloro-4'-biphenylcarboxaldehyde | 0.132-0.193 | 1.1-1.6 |
| Sodium cyanoborohydride (NaCNBH$_3$) in tetrahydrofuran (THF) | 0.03-0.06 NLT 0.6 | 0.75-1.6 |

NLT = not less than.
N/A = not applicable
[a]An additional reagent, sodium borohydride (NaBH$_4$), is used non-stoichiometrically to quench unreacted aldehyde.
[b]Charge factor compensates for consumption of reagents by all reactants: Nucleus factors A, B, C, and D.
[c]Calculated using the charge factor for concentration.

A. Reductive Alkylation

A solution of nucleus factor B (typically 20-45 kg) and copper (II) acetate in methanol was mixed at ambient temperature until dissolution to generate the copper complex of nucleus factor B. To this solution was added the starting material 4-chloro-4'-biphenyl carboxaldehyde, either as a solid or a solution in tetrahydrofuran, followed by a solution of sodium cyanoborohydride in tetrahydrofuran. The solution was heated.

Additional 4-chloro-4'-biphenyl carboxaldehyde was added as necessary to drive the reaction to completion and/or to consume the site-2 mono-alkylated derivative. In-Process Control: Reaction progress was monitored by HPLC against a limit of NMT 1.2% w/w ratio of site-2 mono-alkylated derivative relative to oritavancin.

The reaction mixture was cooled to ambient temperature and terminated by addition of sodium borohydride to convert residual 4-chloro-4'-biphenyl carboxaldehyde to the corresponding alcohol. The sodium borohydride was added in portions, in some instances.

The reaction mixture was adjusted using acetic acid and aqueous sodium hydroxide, as needed. The mixture was concentrated under reduced pressure and acetonitrile was added to precipitate oritavancin as its copper complex. The oritavancin copper complex was collected and washed with a mixture of acetonitrile and methanol, as needed. The wet cake was deliquored for NMT 24 hours at a temperature of NMT 23° C. The wet cake was stored at NMT 8° C.

B. Chromatographic Separation

Oritavancin copper complex was dissolved in a mixture of dilute acetonitrile and aqueous phosphoric acid to de-complex the oritavancin. The de-complexed solution was loaded onto a column containing polystyrene divinylbenzene resin previously equilibrated with a mixture of acetonitrile and aqueous phosphoric acid.

Oritavancin was eluted from the resin by successive application of 14 to 18 v/v % (NLT 2.0 BV bed volumes) and 24 to 27 v/v % acetonitrile in aqueous ammonium phosphate. The eluate was collected in bulk fractions. Consecutive bulk fractions containing oritavancin were sampled to create composite sample pools for testing.

In-Process Control: Composite sample pools were analyzed by HPLC against the pool specifications in Table 9. Bulk fractions that were sampled to constitute a passing composite sample pool were combined.

C. Concentration (UF/DF)

The pooled fractions were concentrated by ultrafiltration and then diafiltered using purified water. The concentrate was further concentrated by ultrafiltration, as needed. The concentrate was diluted with purified water, as needed.

The concentrate pH was adjusted using aqueous phosphoric acid and/or sodium hydroxide solutions, as needed. The oritavancin free base and phosphate concentrations in the concentrate (referred to as retentate) were measured.

In-Process Control: The retentate was analyzed by HPLC against the Retentate Specifications listed in Table 9. The retentate was stored at NMT 25° C. for 8 weeks.

TABLE 9

Chromatography Pool and Retentate Specifications

| Compound | Acceptance Criteria (Peak Area %) |
| --- | --- |
| Nucleus DEV A | NMT 0.90 |
| Oritavancin Factor C | NMT 1.9 |
| RS-K | NMT 0.50 |
| RS-L | NMT 0.90 |
| Oritavancin CR | NMT 1.0 |
| RS-N | NMT 0.60 |
| RS-O | NMT 0.90 |
| RS-M | NMT 0.90 |
| Oritavancin F | NMT 0.40 |
| Specified RS-E/G | NMT 0.8 |
| Single Largest Unspecified Impurity (SLUI) | NMT 0.40 |
| Total Impurities | NMT 6.6 |
| Total Unspecified Impurities | NMT 1.1 |

NMT = not more than.
RS = related substance

D. Salt Crystallization & Drying

The concentrate was heated and ethanol was added to obtain a solution containing 40 to 70 v/v % ethanol. A solution of aqueous ammonium phosphate was added. The solution was seeded with oritavancin diphosphate. The mixture was cooled and a second portion of aqueous ammonium phosphate solution was added. The suspension was cooled further and the crystals were isolated. The cake was washed with not less than 1 L of aqueous ethanol per kilogram of oritavancin free base as measured in the retentate. The solid may be isolated and washed in portions, as needed.

The cake was dried at reduced pressure at NMT 40° C. and sampled for moisture and residual solvents. Drying was monitored by Karl Fischer against a limit of NMT 4.0% w/w water; and by GC against a limit of NMT 5.0% w/w ethanol. The cake was further dried as needed at NMT 40° C. for NMT 7 days. The dried material was mechanically delumped, as needed.

Figure 7B:
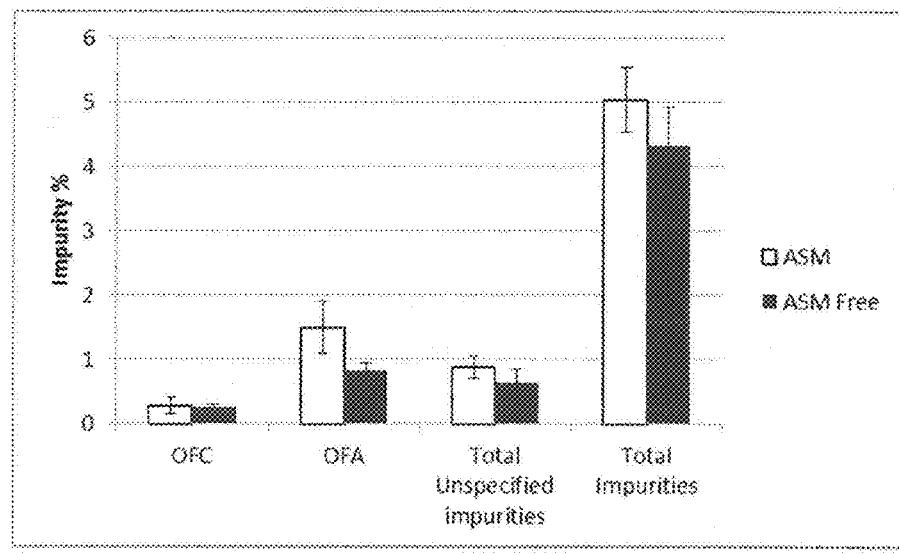

The levels of impurities in the dried material were determined via HPLC. As can be seen in FIG. 7B, the levels of impurities were reduced when the production of oritavancin was initiated with nucleus factor B that had been produced in ASM-free media.

The overall yield of oritavancin diphosphate from nucleus factor B was typically 45 to 72%.

4) Reprocessing Procedures
A. Manufacture of Nucleus Factor B

The following reprocessing procedures were developed for: 1) an impurity specification failure; 2) a phosphate failure; 3) a residual solvents failure; and 4) an inert particulate contamination. One or more similarly impacted batches may be combined for reprocessing.

Reprocess for Impurities

Fraction pools that fail in-process acceptance criteria were reprocessed by repeating the Chromatographic Separation, Concentration, Salt Precipitation and Drying steps.

Reprocess for Phosphate

A phosphate failure at any stage was reprocessed by continuing, or repeating as appropriate, the alkaline diafiltration until a passing in-process phosphate result was obtained. Further downstream processing was performed as described previously.

Reprocess for Insoluble Extraneous Matter Contamination

Nucleus factor B was reprocessed for inert particulate contamination, as needed, by dissolution in water, filtration and re-introduction into the process at the salt precipitation and repeating the drying.

B. Manufacture of Oritavancin Diphosphate (Alkylation)

The following reprocessing procedures were developed for: 1) Drug substance retentate that fails analysis; 2) Oritavancin diphosphate that fails for extraneous matter; and 3) Oritavancin diphosphate that fails for purity. One or more similarly impacted batches may be combined for reprocessing.

Reprocessing of Pool or Retentate for Impurities

A chromatography pool or UF retentate that fails the acceptance criteria for related and specified substances listed in Table 9 was reprocessed.

The pool was carried through the diafiltration process. The chromatographic separation was repeated and fractions were collected, sample composite pools analyzed and acceptable bulk fractions pooled. If acceptable against the specification in Table 9, the reprocessed material was taken forward into the salt crystallization and drying.

Reprocess for Extraneous Material

Oritavancin diphosphate drug substance that fails for a non-purity related specification such as clarity, residue on ignition, or insoluble extraneous matter, was reconstituted to the retentate stage and reprocessed.

The oritavancin diphosphate was dissolved in purified water. If necessary, the pH was adjusted with aqueous phosphoric acid and ammonia water. The solution was filtered and the salt crystallization and drying steps were performed as previously described.

Drug Substance Reprocess for Impurities

Oritavancin diphosphate drug substance that fails purity can also be reprocessed. The oritavancin diphosphate was dissolved in purified water and a mixture of acetonitrile in aqueous phosphoric acid and loaded onto resin. The chromatographic separation was performed and fractions were collected, sample composite pools analyzed and acceptable bulk fractions were pooled. UF concentration was performed and the reprocessed material was analyzed against the retentate specifications listed in Table 9. If acceptable, the reprocessed material was processed forward to the crystallization and drying steps as previously described.

5) Description of Manufacturing Process and Process Controls

The Oritavancin for Injection drug product was manufactured, tested, and primarily packaged using standard processing techniques.

The manufacturing process is scalable and reproducible and comprises the following steps:
  Equilibration of Oritavancin Drug Substance
  Preparation of Oritavancin Bulk Drug Product Solution
  Pre-filtration and Bioburden Reduction
  Component Preparation
  Aseptic Filtration and Filling
  Lyophilization and Stoppering
  Capping and Bulk Packaging
  Secondary Packaging A flow chart summarizing the commercial manufacturing procedure is presented in FIG. 6. The equipment used is listed in Table 10.

TABLE 10

Equipment used for Manufacture of Oritavancin for Injection

| Process Step | Equipment |
|---|---|
| Preparation of Oritavancin Bulk Solution | Solution preparation system with mixers and mixing tanks |
| Preparation of Components | Autoclave |
| | Vial washer |
| | Dry sterilization and depyrogenation oven |
| | Laminar flow heat depyrogenation tunnel |
| Aseptic Filtration and Filling | Sterilizing Filters (0.22 μm membrane) |
| | Filling machine |
| Lyophilization and Capping | Freeze dryers |
| | Capping machine (LAF in Class D supporting area) |

Equilibration of Oritavancin Drug Substance

In one example, the drug substance container was equilibrated from 2-8° C. to room temperature (15-25° C.) prior to weighing. Weighing was performed in a humidity controlled environment such as an insulator.

Preparation of Oritavancin Bulk Drug Product Solution

Water for Injection (WFI) was added in an amount equivalent to approximately 85% of the bulk solution final q.s. weight to a tared compounding vessel. The whole solution preparation phase was performed at 15-30° C. temperature. While mixing, phosphoric acid solution (6% w/v) was added and the pH of the contents was adjusted to 2.8 to 3.0.

Mannitol was added to the compounding vessel and mixed until dissolved, as determined by visual examination. Oritavancin diphosphate was slowly added to the compounding vessel in portions with a mix rate that avoided excess foaming. The solution pH was checked and adjusted to pH 3.6 to 3.8 with diluted phosphoric acid solution after each API addition. Mixing was continued if necessary until the oritavancin diphosphate was dissolved, as determined by visual examination.

WFI was added until the final weight was reached. The solution was mixed and a final pH check was performed, and pH was adjusted to pH 3.6 to 3.8, as needed with diluted phosphoric acid solution. The bulk solution was sampled for appearance, pH and bioburden test.

Pre-Filtration and Bioburden Reduction

The bulk solution was filtered through a 0.45 μm and 0.22 μm filter (bioburden reduction) attached in series. The filtered solution was collected in a suitable size stainless steel tank and held at 15-30° C. The bulk hold time between the API addition and the start of lyophilization was not more than the period validated.

Component Preparation

The glass vials were loaded into a validated tunnel. Initially, they were washed and then depyrogenated in order to obtain a 3 log reduction in endotoxin levels. The stoppers were sterilized and dried in the autoclave as per the validated cycle. Sterilization of filters and other small parts was performed in Sterile Area 3 autoclave as per the validated cycle. Lyophilization trays were depyrogenated in an oven as per the validated cycle with the following settings:

Temperature set point: 220° C.
Process temperature range: 210° C.-250° C.
Depyrogenation time: 300 minutes All connections made to the final bulk container, filtration equipment and filling syringes were performed aseptically in Grade A (Class 100) area.

Aseptic Filtration and Filling

Immediately before filling, the final bulk drug product solution was filtered by passing the solution through two 0.22 μm filters connected in series. In process samples for appearance, density, and bioburden were taken before the beginning of sterilizing filtration. Using aseptic filling procedures in a Grade A environment (Class 100), a target fill weight of 13.51 g of sterile solution was filled into each sterilized vial.

Fill weight checks were performed prior to and during the filling process to verify accuracy. After filling, stoppers were placed partially on the vials.

Lyophilization and Stoppering

Following filling, the vials were transferred into the lyophilizer and subjected to the pre-defined freeze drying cycle. At the end of cycle, the vials were fully stoppered in the lyophilizer. The lyophilization parameters are listed in Table 11. The time between the start of sterile filtration and start of lyophilization was not more than 24 hours.

Capping and Bulk Packaging

The vials were transported to an appropriate capping machine where the vials were capped under LAF Grade A air supply. After capping, vials were collected in a Grade D environment. The lot number was ink-jetted on the crimp. The vials were visually inspected and bulk packaged.

TABLE 11

Summary of Lyophilization Parameters

| Step | Shelf Temp (° C.) ± 3° C. | Pressure (μbar) | Time (h:min) |
|---|---|---|---|
| Load | 5 | Atmospheric | N/A |
| Freezing | 5 to −40 | Atmospheric | 02:00 |
| Freezing | −40 | Atmospheric | 06:00 |
| Evacuation | −40 | 133 | N/A |
| Primary Drying | −40 to −15 | 133 | 02:00 |
| Primary Drying | −15 | 133 | 64:00 |
| Secondary Drying | −15 to 35 | 133 | 02:00 |
| Secondary Drying | 35 | 133 | 07:00 |
| Secondary Drying | 35 to 25 | 133 | 00:30 |
| Secondary Drying | 25 | 133 | 00:30 |
| Pre-Aeration (Nitrogen) | 25 | $0.83 \times 10^6$ | N/A |
| Stoppering | 25 | $0.83 \times 10^6$ | N/A |
| Aeration | 25 | Atmospheric | N/A |
| Preservation | 20 | Atmospheric | N/A |

The levels of impurities in the lyophilized material were determined via HPLC. For oritavancin drug product produced from oritavancin drug substance that had itself been produced via an ASM-free process, the levels of all impurities and of unspecified impurities were 3.6±0.43% and 2.4±0.37% respectively. For oritavancin drug product produced from oritavancin drug substance that had itself been produced via an ASM containing process, the same levels were 4.2±0.71% and 2.9±0.27% respectively.

In-Process Controls

The In-Process Controls are indicated in the schematic flow diagram of the manufacturing process (FIG. 6). The in-process control methods and limits are tabulated in Table 12.

TABLE 12

Summary of In-Process Controls for Oritavancin Drug Product Manufacture

| Process Step | In-process Control Test | Limits | Method Reference |
|---|---|---|---|
| Pre-QS | pH* | 3.6-3.8 | Ph. Eur. |
| Final bulk solution (compounding tank after reaching the final volume) | pH | 3.6-3.8 | USP/Ph. Eur. |
| | Appearance | Clear solution | Visual |
| | Bioburden | ≤10 CFU/100 mL | USP/Ph. Eur. |
| Final bulk solution (before sterilizing filtration) | Appearance | Clear solution | Visual |
| | Density | 0.98-1.02 g/mL at 25° C. | USP |
| | Bioburden | ≤10 CFU/100 mL | USP/Ph. Eur. |
| Filling process | Filling weight | Target: 13.51 g Range: 13.00-14.03 g | Weight measurement |

*The pH of the solution is adjusted in production to a target of 3.7 using dilute phosphoric acid solution via titration after each API addition.

While the invention has been described with reference to certain particular embodiments thereof, those skilled in the art will appreciate that various modifications may be made without departing from the spirit and scope of the invention. The scope of the appended claims is not to be limited to the specific embodiments described.

All patents and publications mentioned in this specification are indicative of the level of skill of those skilled in the art to which the invention pertains. Each cited patent and publication is incorporated herein by reference in its entirety.

What is claimed is:

1. A pharmaceutical composition comprising an oritavancin drug substance preparation and one or more pharmaceutically acceptable excipients, wherein the oritavancin drug substance preparation has about 90% purity or greater by peak area relative to impurities 2-16, defined by peaks B-P of FIG. 2, respectively.

2. The pharmaceutical composition of claim 1, wherein the oritavancin drug substance preparation has about 95% purity or greater by peak area.

3. The pharmaceutical composition of claim 1, wherein the one or more pharmaceutically acceptable excipients are selected from the group consisting of mannitol, sorbitol, sucrose and trehalose.

4. The pharmaceutical composition of claim 1, wherein the pharmaceutically acceptable excipient is mannitol.

5. The pharmaceutical composition of claim 1, wherein the ratio of the drug substance preparation to the one or more excipients is 2:1 by weight.

6. The pharmaceutical composition of claim 1, wherein the purity level of the oritavancin drug substance preparation is measured by HPLC.

7. The pharmaceutical composition of claim 6, wherein the purity level of the oritavancin drug substance preparation is measured by HPLC, and wherein the HPLC measurement utilizes a C18 reverse-phase stationary phase and a gradient of mobile phase B, which is phosphoric acid/water/acetonitrile/tetrahydrofuran at a ratio of about 1/1000/1500/25 (v/v/v/v), in mobile phase A, which is phosphoric acid/water/tetrahydrofuran at a ratio of about 1/1000/10 (v/v/v).

8. A pharmaceutical composition comprising an oritavancin drug substance preparation and one or more pharmaceutically acceptable excipients, wherein the oritavancin drug substance preparation has a maximum impurity level of not more than 4.8% by peak area of impurity 2 and impurity 10, defined by peaks B and J shown in FIG. 2, respectively.

9. The pharmaceutical composition of claim 8, wherein the oritavancin drug substance preparation has a maximum impurity level of not more than 3.0% by peak area.

10. The pharmaceutical composition of claim 8, wherein the oritavancin drug substance preparation has a maximum impurity level of not more than 1.9% by peak area of impurity 2 and 2.9% by peak area of impurity 10.

11. The pharmaceutical composition of claim 8, wherein the one or more pharmaceutically acceptable excipients are selected from the group consisting of mannitol, sorbitol, sucrose and trehalose.

12. The pharmaceutical composition of claim 8, wherein the pharmaceutically acceptable excipient is mannitol.

13. The pharmaceutical composition of claim 8, wherein the ratio of the drug substance preparation to the one or more excipients is 2:1 by weight.

14. The pharmaceutical composition of claim 8, wherein the purity level of the oritavancin drug substance preparation is measured by HPLC.

15. The pharmaceutical composition of claim 14, wherein the purity level of the oritavancin drug substance preparation is measured by HPLC, and wherein the HPLC measurement utilizes a C18 reverse-phase stationary phase and a gradient of mobile phase B, which is phosphoric acid/water/acetonitrile/tetrahydrofuran at a ratio of about 1/1000/1500/25 (v/v/v/v), in mobile phase A, which is phosphoric acid/water/tetrahydrofuran at a ratio of about 1/1000/10 (v/v/v).

* * * * *